(12) United States Patent
Abe et al.

(10) Patent No.: US 9,834,723 B2
(45) Date of Patent: Dec. 5, 2017

(54) PENTAARYLBIIMIDAZOLE COMPOUND AND PRODUCTION METHOD FOR SAID COMPOUND

(71) Applicant: KANTO KAGAKU KABUSHIKI KAISHA, Tokyo (JP)

(72) Inventors: Jiro Abe, Kawasaki (JP); Hiroaki Tamashita, Zama (JP); Kazuhiko Tsutiya, Soka (JP); Takayoshi Suga, Tokyo (JP)

(73) Assignee: KANTO KAGAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/129,812

(22) PCT Filed: Mar. 26, 2015

(86) PCT No.: PCT/JP2015/059290
§ 371 (c)(1),
(2) Date: Sep. 27, 2016

(87) PCT Pub. No.: WO2015/147126
PCT Pub. Date: Oct. 1, 2015

(65) Prior Publication Data
US 2017/0130124 A1 May 11, 2017

(30) Foreign Application Priority Data

Mar. 28, 2014 (JP) ................... 2014-083158

(51) Int. Cl.
*C09K 9/02* (2006.01)
*C08K 5/3445* (2006.01)
(Continued)

(52) U.S. Cl.
CPC .............. *C09K 9/02* (2013.01); *C07D 233/58* (2013.01); *C07D 233/64* (2013.01);
(Continued)

(58) Field of Classification Search
CPC ...... C09K 9/02; C08K 5/3445; C08K 5/3447; C07D 233/58; C07D 233/64; C07D 487/20; G02B 5/23; G02B 5/223
(Continued)

(56) References Cited

U.S. PATENT DOCUMENTS 7,851,132 B2   12/2010   Kawauchi
9,040,647 B2    5/2015   Abe et al.
2011/0306743 A1 12/2011  Abe et al.

FOREIGN PATENT DOCUMENTS

JP   H8-245579 A   9/1996
JP   H8-292573 A   11/1996
(Continued)

OTHER PUBLICATIONS

Hiroaki Yamashitaa and Jiro Abe, Pentaarylbiimidazole, PABI: an easily synthesized fast photochromic molecule with superior durability, Chem. Commun., 2014, 50, 8468-8471. This journal is © The Royal Society of Chemistry 2014.*
(Continued)

*Primary Examiner* — Bijan Ahvazi
(74) *Attorney, Agent, or Firm* — Maschoff Brennan

(57) ABSTRACT

In order to address the problems of conventional photochromic compounds, which are the insufficient coloring/discoloring speed and durability exhibited thereby and the large number of production steps, the present invention provides a photochromic compound that exhibits a high speed coloring/discoloring reaction and high durability while it is able to be synthesized in low cost, and that has industrial applicability. The compound of the present invention is characterized by the insertion of a diarylimidazolyl radical into the ortho position of an aryl group. The compound exhibits photochromic properties, and achieves a photochromic compound having both a high speed color switching reaction and
(Continued)

high durability. Furthermore low cost synthesis is possible, and the photochromic compound has industrial applicability.

16 Claims, 5 Drawing Sheets

(51) Int. Cl.
| | |
|---|---|
| C08K 5/3447 | (2006.01) |
| C07D 233/58 | (2006.01) |
| C07D 233/64 | (2006.01) |
| C07D 487/20 | (2006.01) |
| G02B 5/23 | (2006.01) |
| G02B 5/22 | (2006.01) |

(52) U.S. Cl.
CPC .......... *C07D 487/20* (2013.01); *C08K 5/3445* (2013.01); *C08K 5/3447* (2013.01); *G02B 5/223* (2013.01); *G02B 5/23* (2013.01); *C09K 2211/1007* (2013.01); *C09K 2211/1029* (2013.01); *C09K 2211/1044* (2013.01)

(58) Field of Classification Search
USPC .............. 252/586; 526/219.6, 259; 548/110, 548/314.4, 343.5
See application file for complete search history.

(56) References Cited

FOREIGN PATENT DOCUMENTS

| | | |
|---|---|---|
| JP | 2000-112074 A | 4/2000 |
| JP | 2005-215640 A | 8/2005 |
| JP | 2005-266608 A | 9/2005 |
| JP | 2005-309442 A | 11/2005 |
| JP | 2005-325087 A | 11/2005 |
| JP | 2008-89789 A | 4/2008 |
| JP | 2012-201655 A | 10/2012 |
| JP | 2012-214622 A | 11/2012 |
| JP | 2013-180996 A | 9/2013 |
| JP | 2014-19670 A | 2/2014 |
| WO | 2010/061579 A1 | 6/2010 |
| WO | 2011/070942 A1 | 6/2011 |

OTHER PUBLICATIONS

Fujita, K., et al., "Photochromism of a Radical Diffusion-Inhibited Hexaarylbiimidazole Derivative with Intense Coloration and Fast Decoloration Performance", Organic Letters, vol. 10, Issue 14, 2008, pp. 3105-3108.

Greene, T.W., and Wuts, P.G.M., "Protective Groups in Organic Synthesis", 2nd Edition, 1991, pp. 185-195.

Hayashi, T., Maeda, K. "Preparation of a New Phototropic Substance", Bulletin of the Chemical Society of Japan, vol. 33, No. 4, 1960, pp. 565-566.

* cited by examiner

PENTAARYLBIIMIDAZOLE COMPOUND AND PRODUCTION METHOD FOR SAID COMPOUND

FIELD OF THE INVENTION

The present invention relates to a pentaarylbiimidazole compound and a method for producing the same. More particularly, it relates to a pentaarylbiimidazole compound that possesses characteristics of high speed color switching, high durability, low cost in manufacture and ability of precisely controlling coloring tone and density. Furthermore, it relates to a method for producing the compound that is with a high degree of freedom for molecular design and synthesis.

BACKGROUND OF THE INVENTION

Hexaarylbisimidazole (hereinafter also called 'HABI') (Non-Patent Document 1), diarylethene (Patent Document 1), spirooxazine (Patent Document 2), etc. are known as photochromic compounds which possess characteristic of photochromism. Since these compounds possess the characteristic of color reversal when being irradiated by light, the research of the compounds has been actively carrying out aiming to an application as taking the compounds as light control materials (Patent Document 3) or photorecording materials (Patent Documents 4 and 5).

Hexaarylbisimidazole (HABI) generates a triarylimidazoleyl radical (hereinafter also called a 'TAIR'), which is a highly reactive radical material when irradiated by UV and is therefore conventionally widely used as a photopolymerization initiator (Patent Documents 6 to 8).

The photochromic compounds is well-known as P-type photochromic compounds and T-type photochromic compounds. After being isomerized when irradiated by light, the P-type photochromic compounds can reversibly recover to the original structure by irradiation of light having wavelength different from the previous irradiated light. The T-type photochromic compounds, after being isomerized when irradiated by light, can reversibly recover to the original structure by applying a thermal reacting process for a time period from several minutes to several hours.

However, it is with a drawback that it is necessarily to take a time period from at least several minutes to several hours for performing discoloring reaction since these known conventional photochromic compounds need to transform between isomers of different structures. Furthermore, the conventional HABI has another problem that since a carbon-nitrogen bond is cleaved to generate two triarylimidazoleyl radicals and then the two triarylimidazoleyl radicals will diffuse in medium in such a manner that it takes time for the recombination of radicals, therefore slowing the discoloring reaction rate and lowering the long-term stability such as repetition durability.

In one attempt to solve these problems, it has disclosed a synthesis procedure that two triarylimidazoleyl radical molecules are introduced into the 1- and 8-positions of naphthalene (1,8-NDPI-TPI-naphthalene) (Non-Patent Document 2). It conjugates the solely two naphthalene skeletons and an imidazoleyl radical to form a resonant structure so as to stabilize the chromogen, thereby suppressing the diffusion of radicals. However, not only the above attempt cannot fully satisfy the requirement for discoloring speed but also it has a problem that the chromogen, which is a stabilized radical material, will extract hydrogen from a surrounding medium to thus cause degradation.

Furthermore, there is another method to solve this problem. It has disclosed a synthesis procedure that a triarylimidazoleyl radical is introduced into the paracyclophane introduces to synthesis pseudogem-bisDPI [2.2]paracyclophane (Patent Document 9). The two triarylimidazoleyl radical (TAIR) is bound by using a bridging group which is not conjugated with TAIR to thus it enhances a higher thermal stability, an excellently long-term stability, a high speed of discoloring and higher density coloring. However it can not fully satisfy the requirement of high speed for color switching and of higher density for coloring.

Furthermore, there are a plurality of manufacturing processes required and the material of [2.2]paracyclophane is expensive such that the manufacturing cost thereof is high to thus cause a problem in view of the industrial utility.

Moreover, it has disclosed a synthesis procedure that synthesizes two triarylimidazoleyl radical (TAIR) by use of a conjugated bridging group to control coloring density and discoloring speed after a visible light is emitted thereon (Patent Document 10). In spite that it applies a light having a wide range of visible spectrum to thus achieve a high coloring density, it has the same problem as the pseudogem-bisDPI [2.2]paraclophane that it is incapable of fully satisfying the requirement of high speed for color switching and of higher density for coloring.

PRIOR ART DOCUMENTS

Patent Document 1: JP-A-2005-325087
Patent Document 2: JP-A-2005-266608
Patent Document 3: JP-A-2005-215640
Patent Document 4: JP-A-2000-112074
Patent Document 5: JP-A-08-245579
Patent Document 6: JP-A-2008-089789
Patent Document 7: JP-A-2005-309442
Patent Document 8: JP-A-08-292573
Patent Document 9: WO2010/061579
Patent Document 10: JP-A-2012-201655
Non-Patent Document 1: Hayashi, T.; Maeda, K., Bull. Chem. Soc. Jpn. 1960, 33, 565-566.
Non-Patent Document 2: Fujita, K.; Hatano, S.; Kato, D.; Abe, J., Org. Lett. 2008, 10, 3105-3108.

SUMMARY OF THE INVENTION

To achieve the above objects, the present invention provides an industrial usage of photochromic compound having two characteristics of high speed color switching and high durability while it is able to be synthesized in low cost.

After carrying out an intensive research in order to solve the above-mentioned problems, the present inventors have found that, by introducing diarylimidazolyl radical to ortho positions of aryl group, the compound obtains a photochromic characteristic and further obtains characteristics of high speed color switching reaction and high color density.

The compound of the present invention therefore can be synthesized with less quantity of procedures and the material used is with lower price. Therefore, after a further research, the present invention has been accomplished.

That is, the present invention relates to:

[1] a compound represented by the following general formula (1):

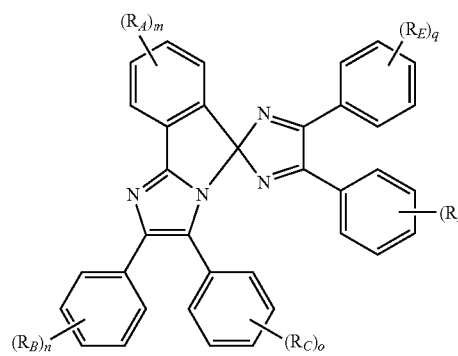 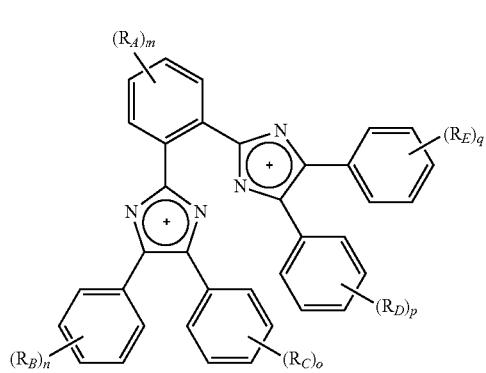

(1)

wherein, in the formula,
the five aryl groups may or may not have substituents $R_A$ to $R_E$,
in is an integer from 1 to 4,
n to q are independent to each other and are integers from 1 to 5,
the substituents $R_A$ are independent to each other and identical to or different from each other in which the substituent(s) $R_A$ is selected one or more from a group consisting of:
hydrogen atom, halogen atom, nitro group, cyano group, trifluoromethyl group, hydroxyl group, thiol group, amino group, diphenylamino group and carbazole group, alkyl group, alkylamino group and alkoxy group with straight chain or with branched chain having carbon number from 1 to 20, $-Y_1-SiZ_1Z_2Z_3$ group, $-Y_1-SiY_2Z_1Z_2$ group and $-Y_r\ SiY_2Y_3Z_1$ group, wherein $Y_1$ to $Y_3$ and $Z_1$ to $Z_3$ are independent to each other and are identical to or different from each other, and $Y_1$ to $Y_3$ represent alkyl group or alkylene group with straight chain or with branched chain having carbon number from 1 to 20, and $Z_1$ to $Z_3$ represent hydrogen atom or halogen atom or alkoxy group with straight chain or branched chain alkoxy group, and
alicyclic ring, heterocyclic ring and aromatic ring which are formed by binding the substituents $R_A$ with each other,
the substituents $R_B$ to $R_E$ are independent to each other and are identical to or different from each other, and are substituents with the same definition as the previous substituents $R_A$ and selected one or more substituents from the group consisting of substituent represented by the following structure formula (i):

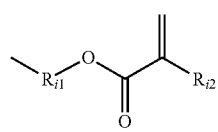

(i)

wherein, in the formula, $R_{i1}$ isalkylene group or alkoxylene group having carbon number from 1 to 4, $R_{i2}$ is hydrogen atom or alkyl group having carbon number from 1 to 3, the substituent having the aryl group forms together with the binding carbon atom(s) and other substituent(s) to thus form or not form an aliphatic or aromatic ring, in which the ring thereof further may or may not have a substituent with the same definition as the previous substituent having the aryl group.

[2] The compound as claimed in [1], wherein the structure of a diarylimidazole moiety at one side and the structure of a diarylimidazole moiety at the other side are different and asymmetric to each other.

[3] The compound as claimed in [1] or [2], wherein each substituent $R_A$ to $R_E$ is substituent selected one or more from the group consisting of: hydrogen, methyl group, methoxy group, nitro group and cyano group.

[4] A photochromic material comprising the compound as claimed in any one of [1] to [3].

[5] A solvent comprising the compound as claimed in any one of [1] to [3].

[6] A resin comprising the compound as claimed in any one of [1] to [3].

[7] A method for producing the compound as claimed in any one of [1] to [3], comprising an reaction between a compound and a benzyl derivative having 1,2-diketone, wherein the compound is represented by the following general formula (2), and the benzyl derivative having 1,2-diketoneis represented by the following general formula (3) and/or the following general formula (4):

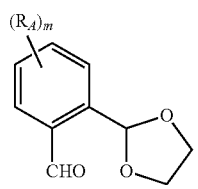

(2)

wherein, in the formula, the aryl group may or may not have substituent $R_A$, and in is an integer from 1 to 4, the substituents $R_A$ are independent to each other and is identical to or different from each other and are substituents with the same definition as the previous substituents $R_A$ in the general formula (1),

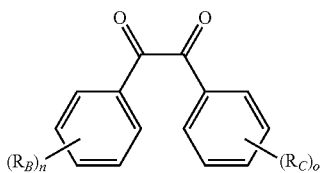

(3)

wherein, in the formula, the two aryl group may or may not have substituents $R_B$ and $R_C$, and n and o are independent to each other, an integer is of from 1 to 5, and the substituent $R_B$ and $R_C$ are, independent to each other and are identical to or different from each other and the substitutent $R_B$ and $R_C$ are substituents with the same definition as the previous substituents $R_B$ and $R_C$ in the general formula (1), and/or
the following general formula (4):

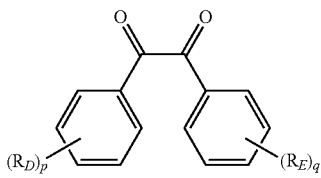

(4)

wherein, in the formula, the two aryl group may or may not have the substituents $R_D$ and $R_E$, and p and q are independent to each other, and are integers from 1 to 5, and the substituent $R_D$ and $R_E$ are independent to each other and are identical to or different from each other and the substituent $R_D$ and $R_E$ are substituents with the same definition as the previous substituents $R_D$ and $R_E$ in the general formula (1).

It should be noted that, in the formula (2), the "h ν→" indicates that the compound of the present invention transfers to a radical material of chromogen having high energy level by absorbing energy such as ultra violet, and "←Δ" indicates that the radical material absorbs thermal energy to reversibly transfer to imidazole dimer having a low energy level.

The compound according to the present invention is characterized that two diarylimidazolyl radical are combined at ortho positions of the aryl groups.

It is difficult to synthesize a compound by introducing two diarylimidazole to nearby positions such as the synthesis of the present invention, since by-products will be produced and the two diarylimidazole are unable to be introduced. In spite that a compound disclosed in the non-patent document 1, the patent document 9 and the patent document 10 has two diarylimidazoles, the two diarylimidazoles are not introduced to two relatively distant positions in molecule.

While the method of the present invention can introduce two arylimidazole to ortho positions. And furthermore, the method of the present invention can also achieve an reaction of one-pot that after one diarylimidazole is introduced into the system, it introduces another diarylimidazole identical to or different from the introduced diarylimidazole.

Compared with a conventional photochromic compound, the compound of the present invention has both high speed color switching characteristics and high color durability. Furthermore, it can be synthesized by fewer manufacturing procedures and cheaper raw material. Therefore, as a result of a further research, the present invention has been accomplished. Furthermore, it achieves the goal of providing a photochromic compound which can be synthesized at low cost and is industrially-applicable.

It can therefore be anticipated that the compound of the present invention will be applied to a wide range of technical fields such as technical fields of security ink, light control materials, holographic materials and optical switch elements.

DETAILED DESCRIPTION OF THE PREFERRED EMBODIMENTS

Figure 1:
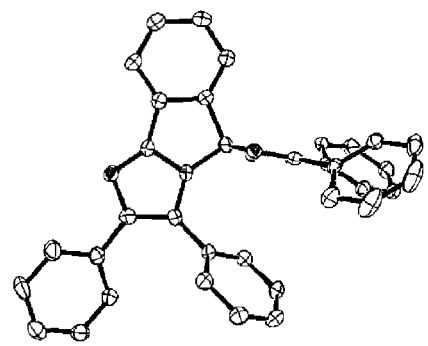
FIG. 1 is a diagram showing the molecular structure of 2,3,4',5'-tetraphenyl-spiro [imidazo [2,1-α]isoindole-5,2'-imidazole] in the embodiment 3, which is elucidated by a structural analysis of single crystal X-ray diffraction.

The follows describes the present invention in detail.

The compound of the present invention is represented by the following general formula (1):

group with straight chain or with branched chain having carbon number from 1 to 20, alkylamino group with straight chain or with branched chain having carbon number from 1 to 20, alkoxy group with straight chain or with branched chain having carbon number from 1 to 20, $-Y_1-SiZ_1Z_2Z_3$ group, $-Y_1-SiY_2Z_1Z_2$ group and $-Y_1-SiY_2Y_3Z_1$ group ($Y_1$ to $Y_3$ and $Z_1$ to $Z_3$ are independent to each other and are identical to or different from each other, $Y_1$ to $Y_3$ represent alkyl group or alkylene group with straight chain or with branched chain having carbon number from 1 to 20, and $Z_1$ to $Z_3$ represent hydrogen atom or halogen atom or alkoxy group with straight chain or with branched chain having carbon number from 1 to 8), ring group mutually bound by aromatic ring, a heterocyclic ring and an alicyclic ring (wherein the aromatic ring includes ring such as benzene ring, naphthalene ring, anthracene ring, the heterocyclic ring includes ring such as pyridine ring, pyrrole ring, furan ring, thiophene ring, and the alicyclic ring includes ring such as cyclopentane ring, cyclohexane ring. One or more substituents may be selected from these substituents.

Furthermore, the substituents $R_B$ to $R_E$ are independent to each other and may be identical to or different from each other. The substituents may be selected from the group consisting of hydrogen atom, halogen atom, nitro group, cyano group, trifluoromethyl group, hydroxyl group, thiol group, amino group, diphenylamino group, carbazole group, alkyl group with straight chain or with branched chain having carbon number from 1 to 20, alkylamino group with straight chain or with branched chain having carbon number from 1 to 20, alkoxy group with straight chain or branched chain from 1 to 20 having carbon number from 1 to 20, $-Y_1-SiZ_1Z_2Z_3$ group, $-Y_1-SiY_2Z_1Z_2$ group and $-Y_1-SiY_2Y_3Z_1$ group ($Y_1$ to $Y_3$ and $Z_1$ to $Z_3$ are independent to each other and are identical to or different from each other, and $Y_1$ to $Y_3$ represent alkyl group or of alkylene Formula (1)

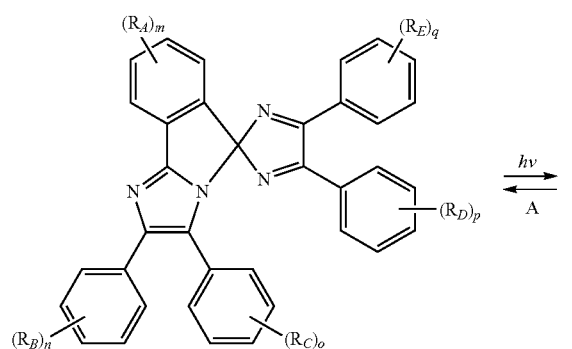
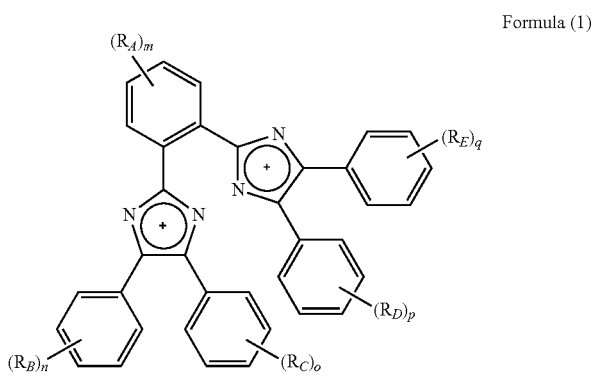

In the aryl groups of the general formula (1), carbon atoms not binding with imidazole ring may have mutual independent substituents $R_A$ to $R_E$, the number in is an integer from 1 to 4, and the number n to q are integers from 1 to 5 which are independent to each other.

The substituents $R_A$ are independent to each other and may be identical to or different from each other. The substituent(s) $R_A$ can be selected from a group consisting of hydrogen atom, halogen atom, nitro group, cyano group, trifluoromethyl group, hydroxyl group, thiol group, amino group, diphenylamino group and carbazole group, alkyl group with straight chain or branch chain having carbon number from 1 to 20, and $Z_1$ to $Z_3$ represent hydrogen atom or halogen atom or alkoxy group with straight chain or with branched chain having carbon number from 1 to 8), ring group mutually bound by aromatic ring, a heterocyclic ring and an alicyclic ring (wherein the aromatic ring includes ring such as benzene ring, naphthalene ring, anthracene ring, the heterocyclic ring includes ring such as pyridine ring, pyrrole ring, furan ring, thiophene ring, and the alicyclic ring includes ring such as cyclopentane ring, cyclohexane ring, and substituents represented by the following structure formula

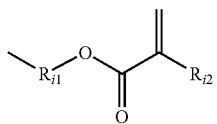

in which, in the partial structure formula (i), $R_{i1}$ is alkylene group or alkoxylene group having carbon number from 1 to 4, $R_{i2}$ is hydrogen atom or alkyl group having carbon number from 1 to 3. One or more substituents may be selected from these substituents.

In view of the compound of the present invention in the general formula (1), the structure of one diarylimidazole moiety of the compound may be the same or be different from another diarylimidazole moiety of the compound. The present invention combines two diarylimidazole radicals having different absorbance wavelengths or introducing the substituent(s) to aryl position of the compound of the present invention to make it possible to more precisely control the photochromic characteristics such as coloring tone or density to thus achieve the goal that can optimally design the molecule structure of the compound corresponding to the applying purpose.

In this case, for the purpose of precisely control photochromic characteristics, the introduced substituents $R_A$ to $R_E$ in view of tone/response rate control are preferably substituents selected from electron-donating group (such as hydrogen, methyl group and methoxy group), nitro group, and cyano group, etc. More preferably, the substituents can be selected from methoxy group and nitro group, etc. One or more substituents may be selected from these substituents.

Furthermore, the compounds of the present invention, acting as a functional moiety, is introduced into the high polymer by means of condensing and polymerizing the polymerizable substituent and the polymerizable functional group, wherein the polymerizable substituent(s) is/are in an amount of one or two which is/are able to be polymerized and is selected from the substituents $R_B$ to $R_E$, and the polymerizable functional group(s) is/are in an amount of one or two which is/are contained in the high polymer main chain or side chain of the high polymer. The same plurality of the compounds of the present invention having more than two polymerizable substituents selected from the substituents $R_C$ to $R_E$ is radically polymerized to thus able to form a chain polymer or reticulated polymer. In this case, as the polymerizable substituents $R_B$ to $R_E$, the substituents are preferably selected from hydroxyl group, amino group, carboxyl group, isocyanate group, halogen group, azide group, vinyl group, ethynyl group, and a group represented by the following partition structure formulae (iv):

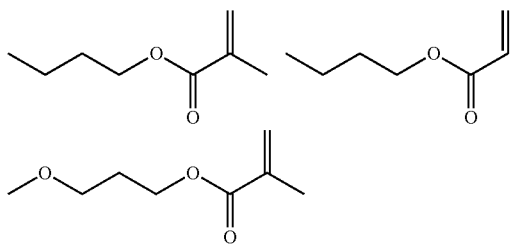

including acrylic acid or methacrylic acid esters such as methacrylate butyl group, acrylate-butyl group or methacrylic acid propoxy group. More preferably, the substituents are selected from hydroxyl group, methacrylate butyl group. One or more of these substituents may be selected for substitution.

Among the above substituents $R_A$ to $R_E$ containing the aryl group of the compounds of the present invention, it defines substituents $R_{x1}$ to $R_{x4}$ which are substituents including substituents having a bridging group and substituents other than the above mentioned substituents which are introduced for purpose of precisely controlling photochromic characteristics and other than the above mentioned substituents which are used for polymerizing the function group containing a high polymer main chain or side chain. The defined substituents $R_{X1}$ to $R_{X4}$ are preferably selected from hydrogen atom, alkyl group with straight chain or with branched chain having carbon number from 1 to 20, etc., and are more preferably selected from a group consisting of hydrogen atom and methyl group. One or more of these substituents may be selected for substitution.

Furthermore, the above substituents are formed by integrally combining (i) the carbon atom binding with the substituents, (ii) substituents other than the above substituents and (iii) the carbon atom binding with substituents other than the above substituents. The integral combination of the all preferably forms heterocyclic ring (such as benzene ring, naphthalene ring, anthracene ring), heterocyclic ring (such as pyridine ring, pyrrole ring, furan ring, thiophene ring), and alicyclic ring [J12] (such as cyclopentane ring, cyclohexane ring). The ring may further contain another substituents which has the same definition as the above substituents containing aryl group. The two diarylimidazole positions of the present invention may be asymmetric to each other according to these ring structures or substituents.

Moreover, in the five aryl groups of the compounds of the present invention, it adjusts a distance, an angle and molecule flexibility of two imidazole rings by use of the number, the type of the substituents and the structure of aromatic ring formed by the substituents to which the five aryl groups of the compounds are bound to thus be possible to appropriately adjust the photochromic characteristics such as color switching reacting speed or coloring density corresponding to the purpose of the compounds for the present invention.

The examples of the specific compounds represented in the general formula (1) are preferably the compound including 2,3,4',5'-tetraphenyl-spiro [imidazo [2,1-α]isoindole-5,2'-imidazole], 2,3,4',5'-tetrakis(4-methoxyphenyl)spiro [imidazo [2,1-α]isoindole-5,2'-imidazole], 7,8-dimethoxy-2,3,4',5'-tetraphenyl-spiro [imidazo [2,1-α]isoindole-5,2'-imidazole] and the derivatives of these compounds.

The high polymer, which is previously mentioned in the present invention, is a high polymer containing, in the main chain and/or the side chain of the high polymer, repeating structural units represented by following partition structure formula (ii):

and/or partition structure formula (iii).

Specifically, in the exemplified repeating structural units, B is one or more than two linking groups selected from the group consisting of carbon atom, nitrogen atom and oxygen atom, F is a derivative of the compound of the present invention, F-B represents a bind between the linking group and one or two substituents selected from substituents $R_C$ to $R_E$ of the derivative of the compound, and α, β, γ, δ and ε are independent to each other and are integers more than 1.

In the compound of the present invention, one or two polymerizable substituent such as hydroxyl group selected from the substituent $R_C$ to $R_E$, can condense and polymerize the linking group which is polymerizable to one or two carboxyl group containing in the main chain or side chain of a high polymer such that the compounds of the present invention can be acted as functional moiety to introduce into the high polymer.

Since the compound of the present invention has a high speed color switching characteristic and a high color density, it also may be mixed with a predetermined solvent. The mixed solvent is preferably benzene, toluene, chloroform, methylene chloride. In view of chromogen stability, benzene and toluene are preferable. A mixture of two or more of these solvents may also be used.

Since the compounds of the present invention has a high speed color switching characteristic and a high color density even in the solid phase of a plastic materials such as resin or glass, it may mix with a solid of a predetermined resin or glass, or may be taken as the functional moiety to chemically bind with in a main chain of the resin. The mixed resin preferably can be polymethyl methacrylate, polystyrene, polyimide, Teflon®, polycarbonate and polyurethane, wherein in a viewpoint of the stability of the color-forming material, the mixed resin may be more preferable as polymethyl methacrylate, a Teflon®, polycarbonate and polyurethane.

The compound of the present invention as used as a photochromic material, solvent and resin containing the compound may be security ink, hologram material, light modulating material and optical switch, etc.

The compound of the present invention is a photochromic compound characterized with in particularly high speed discoloring, and visually photochromic discoloring characteristic being simultaneous with the irradiation light determination.

Regarding discoloring speed of the compound of the present invention, for example, under a measurement that use a benzene solution as a solvent with the concentration of $3.1 \times 10^{-4}$ M and thereafter is measured by nanosecond laser flash photolysis measurement method described later, the half-life of the chromogen is preferably 1~2000 μs, more preferably is 1~1000 μs, and furthermore preferably is in a range of 1~500 μs.

A method for producing the compound of the present invention comprises: reacting a compound represented by the following general formula (3) with a benzyl derivative having 1,2-diketone represented by the following general formula (4) and/or the following general formula (5), (formula 2)

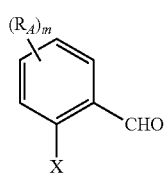

(2)

(formula 3)

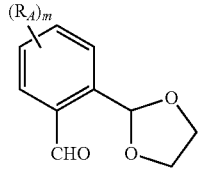

(3)

(formula 4)

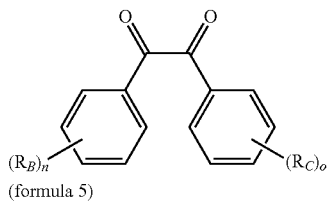

(4)

(formula 5)

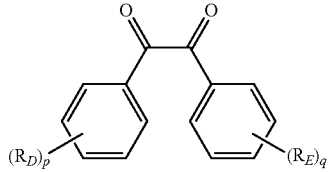

(5)

wherein a compound represented by the following general formula (2) takes a o-halobenzaldehyde body represented by the following general formula (2) as a start compound, aldehyde moiety is protected and thereafter o-position of aldehyde is derivatized to form aldehyde, in the general formula (2) and the general formula (3), the substituents $R_A$ and subscript in respectively have the same definitions as these of the substituents $R_A$ and subscript in defined in the general formula (1), and in the general formula (4) and the general formula (5), the substituents $R_B$ to $R_E$ and the subscript n to q have the same definitions as these of the substituents $R_B$ to $R_E$ and subscript n to q defined in the general formula (1).

EMBODIMENTS

The present invention will be explained more specifically with reference to the embodiments and comparative examples below, but the present invention is not intended to be limited to these examples and various modifications can be made without deviating from the technical spirit of the present invention.

Embodiment 1

Synthesis of 2-(1,3-dioxolan-2-yl)benzaldehyde

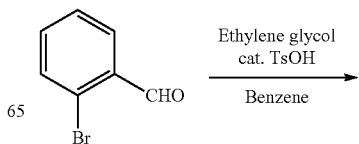

-continued

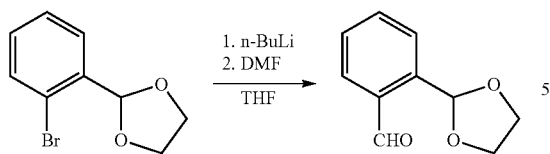

The synthesizing processes of the above includes: placing 2-bromobenzaldehyde 4.97 g (26.9 mmol), ethylene glycol 3.49 g (56.2 mmol) p-toluenesulfonic acid monohydrate 470 mg (2.47 mmol) into a 100 mL two-neck flask, add benzene 10 mL, and refluxing the mixture with Dean-Stark apparatus for 24 hours; after cooling down the temperature to room temperature, terminating the reaction with a saturated sodium bicarbonate aqueous solution and performing an extraction with dichloromethane; drying the organic layer with sodium sulfate and distilling off the solvent under a reduced pressure to obtain a crude product; and performing a purification with silica gel column chromatographic (dichloromethane) to obtain 2-(2-bromophenyl)-1,3-dioxolane 5.01 g (22.1 mmol) in 82% yield. The measurement results of NMR are shown below.

$^1$H NMR (400 MHz, CDCl$_3$): δ=7.61-7.56 (m, 2H), 7.34 (dd, J1=7.5 Hz, J$_2$=7.5 Hz, 1H), 7.24-7.20 7 (in, 1H), 6.11 (s, 1H), 4.17-4.06 (in, 4H)

Dissolving 2-(2-bromophenyl)-1,3-dioxolane 4.83 g of (21.1 mmol) in dehydrated tetrahydrofuran (THF) 15 mL and cooling down the temperature to −78° C.; then adding n-butyllithium hexane solution 1.60M hexane solution 16 mL slowly, and stirring for 2 hours at −78° C.; after raising the temperature to −30° C., cooling down to −78° C. again, and then adding dehydrated dimethylformamide (DMF) 1.3 mL; raising the temperature to room temperature and stirring the mixture for 12 hours; terminating the reaction with saturated sodium bicarbonate aqueous solution, performing an extraction with ethyl acetate, drying the organic layer with sodium sulfate aqueous solution, and distilling the solvent off under a reduced pressure to obtain crude product; and performing a purification with silica gel column chromatography (hexane/ethyl acetate=4/1) to obtain 2-(1,3-dioxolan-2-yl)benzaldehyde 3.61 g (20.2 mmol) in 96% yield.

$^1$H NMR (400 MHz, CDCl$_3$): δ=10.42 (s, 1H), 7.94 (d, J=7.6 Hz, 1H), 7.74 (d, J=7.6 Hz, 1H), 7.62 (dd, J$_1$=7.5 Hz, J$_2$=7.5 Hz, 1H), 7.53 (dd, J$_1$=7.5 Hz, J$_2$=7.5 Hz, 1H), 6.41 (s, 1H), 4.16-4.10 (in, 4H)

Embodiment 2

Synthesis of 1,2-bis(4,5-diphenyl-H-imidazol-2-yl)benzene

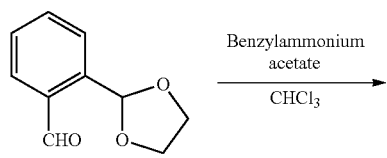

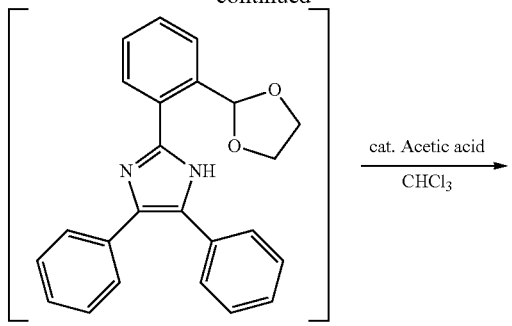

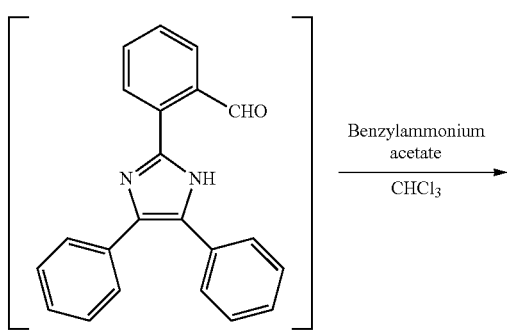

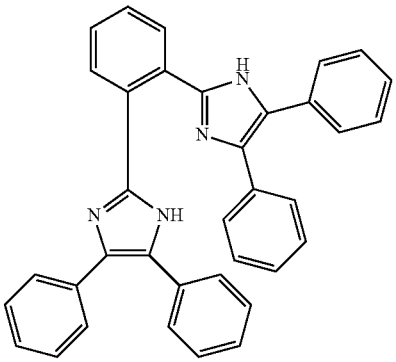

The synthesizing processes of the above includes: placing 2-(1,3-dioxolan-2-yl)benzaldehyde 38.7 mg (2.31 mmol), benzyl 513 mg (2.44 mmol) and ammonium acetate 747 mg (9.69 mmol) in a sealed tube container, and adding chloroform 8 mL, then stirring the mixture for 18 hours at 110° C.; adding benzyl 517 mg (2.46 mmol), ammonium acetate 488 mg (6.33 mmol) and acetic acid 1 mL and then continuously stirring for an additional 24 hours at 110° C., neutralizing the mixture with ammonia water, extracting with chloroform, drying the organic layer with sodium sulfate, distilling off the solvent under a reduced pressure to obtain a crude produce, and performing a recrystallization of chloroform/hexane mixed solvent to obtain 1,2-bis(4,5-diphenyl-1H-imidazol-2-yl)benzene 596 mg (1.16 mmol) in 50% yield.

$^1$H NMR (400 MHz, DMSO-d$_6$): δ=14.08 (s, 2H), 8.19-8.17 (m, 2H), 7.61-7.59 (m, 2H), 7.55-7.41 (m, 10H), 7.30-7.28 (in, 12H).

Embodiment 3

Synthesis of 2,3,4',5'-tetraphenyl-spiro [imidazo [2,1-α]isoindole-5,2'-imidazole]

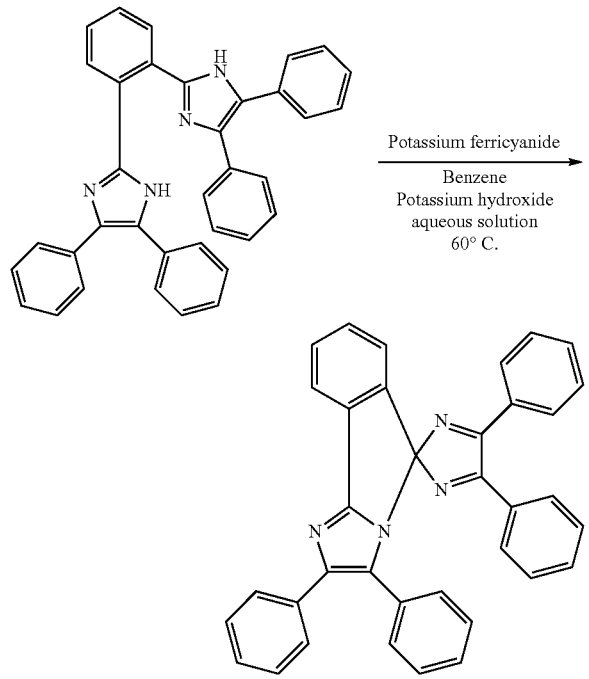

The synthesizing processes of the above includes: suspending 1,2-bis(4,5-diphenyl-1H-imidazol-2-yl)benzene 38.7 mg (0.0752 mmol) in benzene 5 mL, and dissolving potassium ferricyanide 200 mg (3.56 mmol) and potassium hydroxide 745 mg (2.26 mmol) in ion-exchange water 20 mL and adding it back, then stirring the mixture vigorously for 2 hours at 60° C.; after cooling down the temperature to room temperature, placing the mixture in a separatory funnel and washing the organic layer well with ion-exchanged water; and drying the organic layer with sodium sulfate, distilling off the solvent under a reduced pressure to obtain 2,3,4',5'-tetraphenylspiro [imidazo [2,1-α]isoindole-5,2'-imidazole] 34.7 mg (0.0677 mmol) in 90% yield.

$^1$H NMR (400 MHz, CDCl$_3$): δ=8.03 (d, J=7.5 Hz, 1H), 7.57 (d, J=7.1 Hz, 2H), 7.53-7.49 (m, 3H), 7.38-7.35 (m, 4H), 7.30-7.28 (m, 7H), 7.25-7.10 (m, 6H), 6.84 (d, J=6.8 Hz, 1H), ESI-TOF-MS (m/z): 513 [M+H]$^+$

Use single-crystal X-ray structure analyzer mounted with CCD (manufactured by Bruker AXS Co., SMART APEX II) to analyze the crystal structure of synthesized 2,3,4',5'-tetraphenyl-spiro [imidazo [2,1-a]isoindole-5,2'-imidazole]. The molecular structure revealed by the analysis is shown in FIG. 1.

Embodiment 4

Nanosecond laser flash photolysis measurement of 2,3,4',5'-tetraphenyl spiro [imidazo [2,1-α]isoindole-5,2'-imidazole]. The nanosecond laser flash photolysis measurement processes of 2,3,4',5'-tetraphenyl spiro [imidazo [2,1-α]isoindole-5,2'-imidazole] includes: performing the laser flash photolysis measurement of synthesized 2,3,4',5'-tetraphenyl spiro [imidazo [2,1-α]isoindole-5,2'-imidazole] by a time-resolved spectroscopic measurement device (model TSP-1000 which is manufactured by Ltd. Yunisoku); using a quartz spectral cell having an optical path length of 10 mm to perform nanosecond laser flash photolysis measurement of 2,3,4',5'-tetraphenyl spirobenzene [imidazo [2,1-α]isoindole-5,2'-imidazole] benzene solution (the concentration is $3.1 \times 10^{-4}$M) where it is performed under an argon atmosphere and at 25° C.

Figure 2:
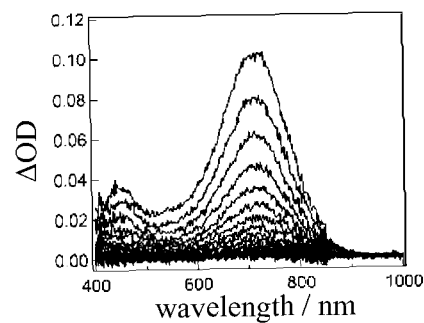
FIG. 2 is a graph showing a visible/near-IR absorption spectrum of chromogen of the compound in the embodiment 3, which is measured by a nanosecond laser flash photolysis, wherein the spectrum is obtained by a measurement every 0.8 μs after the irradiation of a nanosecond laser pulse.

FIG. 2 shows a visible/near-IR absorption spectrum of 2,3,4',5'-tetraphenyl spiro [imidazo [2,1-α]isoindole-5,2'-imidazole] benzene solution, wherein the spectrum is obtained by a measurement every 0.8 μs immediately after the irradiation by using nanosecond ultraviolet laser having a wavelength of 355 nm (pulse width: 5 ns, output: 8 mJ) by means of time-resolved spectroscopy apparatus. From this result, it confirms that 2,3,4',5'-tetraphenyl spiro [imidazo [2,1-α]isoindole-5,2'-imidazole] can reversibly generates a chromogen having a strong absorption band of 710 nm by irradiation with ultraviolet light.

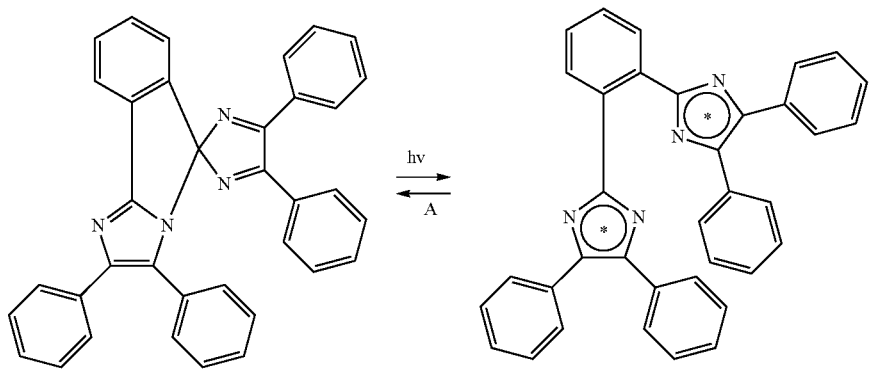

Figure 3:
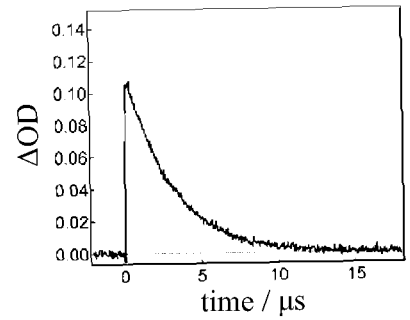
FIG. 3 is a graph showing a decay of absorbing degree in 710 nm for a chromogen of the compound in the embodiment 3, which is measured by a nanosecond laser flash photolysis.

Also, FIG. 3 shows the result of measurement of the time decay relating to the absorption band of 710 nm which appears while the 2,3,4',5'-tetraphenyl spiro [imidazo [2,1-α]isoindole-5,2'-imidazole] benzene solution is irradiated by nanosecond ultraviolet laser having a wavelength of 355 nm (pulse width: 5 ns, output: 4 mJ). As the result, it thus confirms that the chromogen of 2,3,4',5'-tetraphenylspiro [imidazo [2,1-α]isoindole-5,2'-imidazole has a half-life of 2.6 μs after the irradiation is terminated at 25° C. and is attenuated rapidly.

Figure 4:
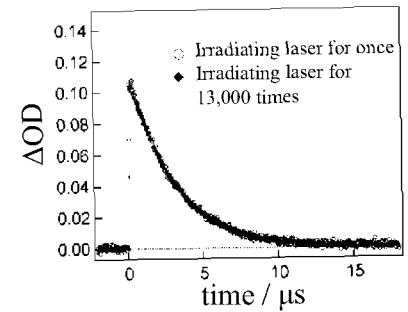
FIG. 4 is a graph showing a decay of absorbing degree in 710 nm for a chromogen of the compound in the embodiment 3, which is measured by irradiating laser pulse for once and irradiating laser pulse for 13,000 times in a measurement of a nanosecond laser flash photolysis.
Figure 5:
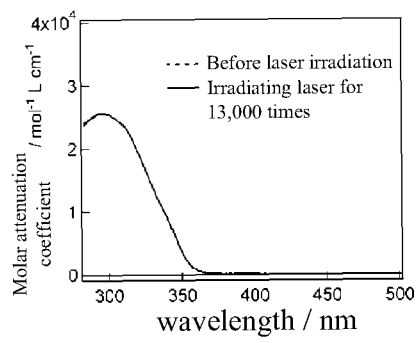
FIG. 5 is a graph showing a UV/visible absorption spectrum of chromogen of the compound in the embodiment 3, which is obtained before a laser irradiation and after laser irradiating for 13,000 times.

Then it performs the durability test by irradiating the 2,3,4',5'-tetraphenyl spiro [imidazo [2,1-α]isoindole-5,2'- imidazole] benzene solution 13000 times by nanosecond ultraviolet laser having a wavelength of 355 nm (pulse width; 5 ns, output: 4 mJ) at 25° C. FIG. 4 illustrates a result of time decay relating to the absorbance of 710 nm by comparing that is irradiated once by the nanoseconds ultraviolet laser and that is irradiated for 13000 times by the nanoseconds ultraviolet laser. It confirms that the time decay relating to the absorbance is kept remained the same and the sample has not been deteriorated even after being irradiated for 13000 times by nanosecond UV laser. In addition, FIG. 5 illustrates the ultraviolet-visible absorption spectrum of 2,3,4',5'-tetraphenyl spiro [imidazo [2,1-α]isoindole-5,2'-imidazole irradiated once by the nanosecond ultraviolet laser and irradiated for 13000 times by the nanosecond ultraviolet laser. And it thus confirms that the ultraviolet-visible absorption spectrum of 2,3,4',5'-tetraphenyl spiro [imidazo [2,1-α]isoindole-5,2'-imidazole after the first irradiation and that after 13000 times of irradiation are kept unchanged. And the result indicates that 2,3,4',5'-tetraphenyl-spiro [imidazo [2,1-α]isoindole-5,2'-imidazole] is a photochromic compound having a high repetition durability.

Embodiment 5

Synthesis of 1,2-bis(4,5-bis(4-methoxyphenyl)-1H-imidazol-2-yl) benzene

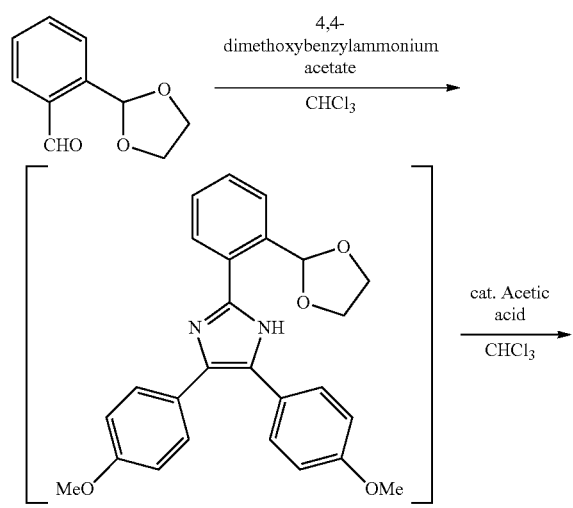

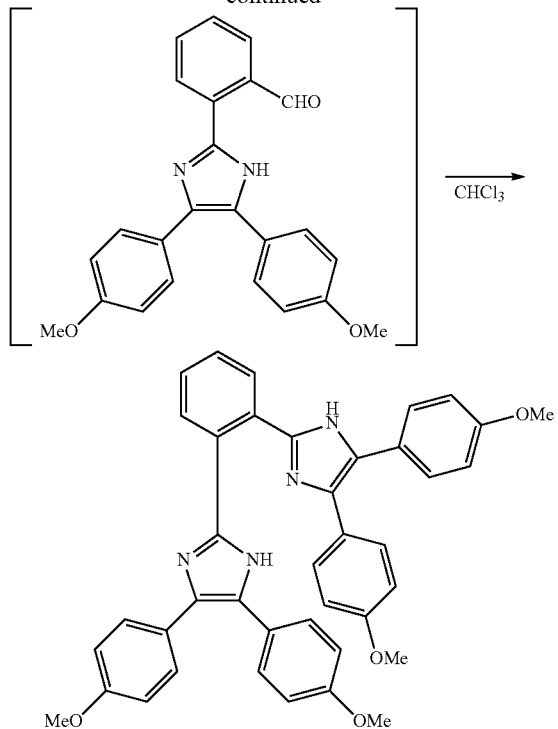

The synthesizing processes of the above includes: placing 2-(1,3-dioxolan-2-yl)benzaldehyde 501 mg (2.81 mmol), 4,4'-dimethoxybenzyl 1.60 g (5.92 mmol) and ammonium acetate 1.21 mg (15.7 mmol) into a sealed tube container, adding chloroform 8 mL and stirring the mixture for 24 h at 110° C.; adding acetic acid 1 mL and continuously stirring for an additional 24 hours at 110° C.; neutralizing the mixture with aqueous ammonia, performing an extraction with chloroform, drying the organic layer with sodium sulfate, and distilling off the solvent under reduced pressure to obtain the crude product; and performing a purification with silica gel column chromatography (hexane/ethyl acetate=1/1) to obtain 1,2-bis (4,5-bis(4-methoxyphenyl)-1H-imidazol-2-yl) benzene 701 mg (1.10 mmol) in 39% yield.

$^1$H NMR (400 MHz, DMSO-$d_6$): δ=14.08 (s, 2H), 8.17-8.15 (m, 2H), 7.57-7.54 (m, 2H), 7.35 (s, 8H), 6.86 (d, J=8.8 Hz, 8H), 3.77 (s, 12H)

Embodiment 6

Synthesis of 2,3,4',5'-tetrakis(4-methoxyphenyl) spiro [imidazo [2,1-α]isoindole-5,2'-imidazole]

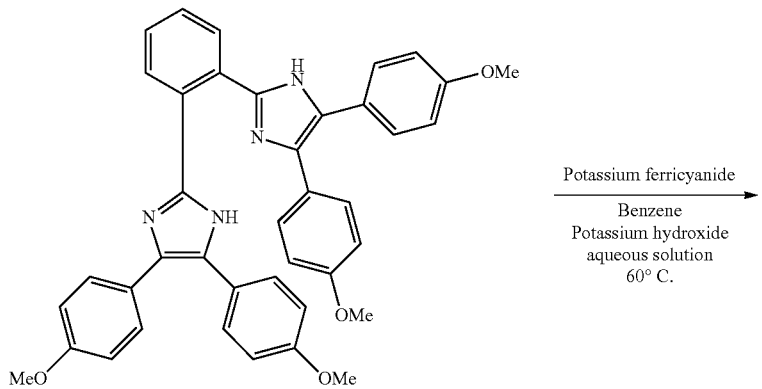

-continued

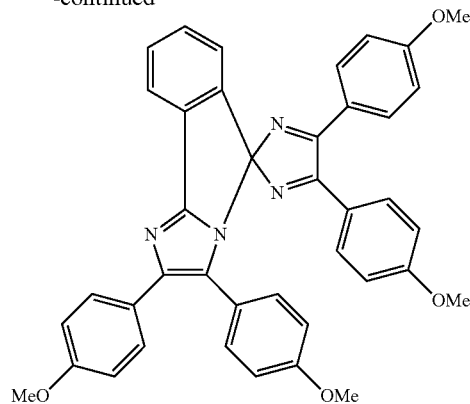

The synthesizing processes of the above includes: suspending 1,2-bis(4,5-bis(4-methoxyphenyl)-1H-imidazol-2-yl)benzene 344 mg (0.542 mmol) in benzene 10 mL, dissolving potassium ferricyanide 1.34 g (4.07 mmol) and potassium hydroxide 406 mg (7.24 mmol) in ion-exchange water 20 mL and adding it back, then stirring the mixture vigorously for 2 hours at 60° C.; after cooling down the temperature to room temperature; and placing the organic layer in a separatory funnel, washing the organic layer well with ion-exchanged water, drying with sodium sulfate, distilling off solvent under reduced pressure to obtain 2,3,4',5'-tetrakis(4-methoxyphenyl)spiro [imidazo [2,1-α]isoindole-5,2'-imidazole] 310 mg (0.49 mmol) in 90% yield.

$^1$H NMR (400 MHz, CDCl$_3$): δ=7.98 (d, J=7.6 Hz, 1H), 7.67-7.63 (m, 1H), 7.53 (d, J=8.9 Hz, 2H), 7.44-7.41 (m, 1H), 7.30 (d, J=5.1 Hz, 5H), 7.26 (d, J=7.7 Hz, 1H), 7.16 (d, J=8.7 Hz, 2H), 7.06 (d, J=8.9 Hz, 4H), 6.90 (d, J=8.9 Hz, 2H), 6.75 (d, J=8.7 Hz, 2H), 3.88 (s, 6H). 3.77 (s, 3H), 3.70 (s, 3H), ESI-TOF-MS (m/z): 633 [M+H]$^+$

Embodiment 7

Nanosecond laser flash photolysis measurement of 2,3,4',5'-tetrakis(4-methoxy-phenyl)spiro [imidazo [2,1-α]isoindole-5,2'-imidazole].

5,2'-imidazole] by using time-resolved spectroscopy measuring device (model TSP-1000 which is manufactured by KK Yunisoku); using a quartz spectral cell having an optical path length of 10 mm to perform nanosecond laser flash photolysis measurement of 2,3,4',5'-tetrakis(4-methoxyphenyl)spiro [imidazo [2,1-α]isoindole-5,2'-imidazole] benzene solution (concentration of 3.3×10$^{-4}$M) and it is performed under an argon atmosphere, and at 25° C.

Figure 6:
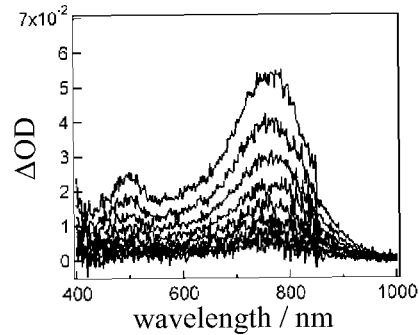
FIG. 6 is a graph showing a visible/near-IR absorption spectrum of chromogen degradation by time of the compound in the embodiment 3, which is measured by nanosecond laser flash photolysis, wherein the spectrum is obtained by a measurement every 1.6 μs after the irradiation of a nanosecond laser pulse.

FIG. 6 shows the results of measurement of visible and near infrared absorption spectrum measurement of 2,3,4',5'-tetrakis(4-methoxyphenyl)spiro [imidazo [2,1-α]isoindole-5,2'-imidazole] benzene solution, wherein the spectrum is obtained by a measurement every 1.6 μs after the irradiation by using nanosecond ultraviolet laser having a wavelength of 355 nm (pulse width: 5 ns, output: 8 mJ) by means of time-resolved spectroscopy apparatus. As the result, it confirms that 2,3,4',5'-tetrakis(4-methoxyphenyl)spiro [imidazo [2,1-α]isoindole-5,2'-imidazole] can reversibly generates a chromogen having a strong absorption band near 750 nm by irradiation by ultraviolet. It also confirms that the maximum absorption wavelength of the chromogen shifts to the longer wavelength side by introducing a methoxy group to the phenyl group of 4,5-position of the imidazole ring.

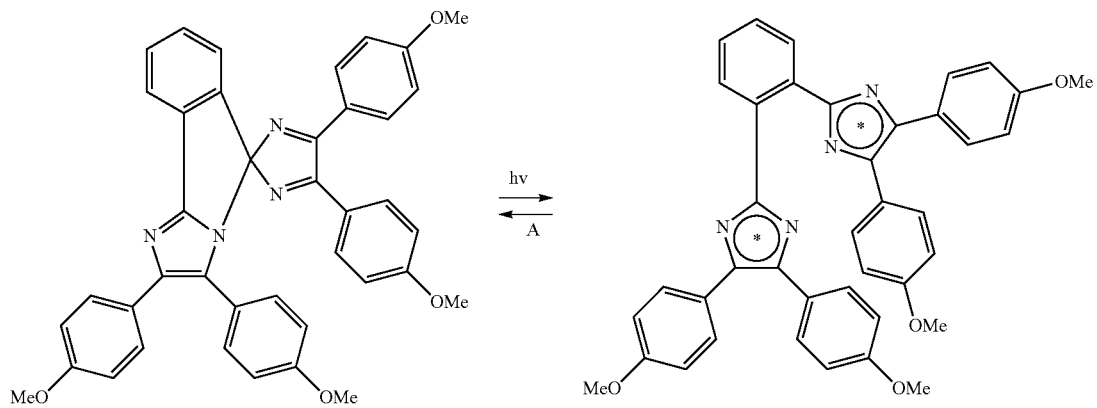

Figure 7:
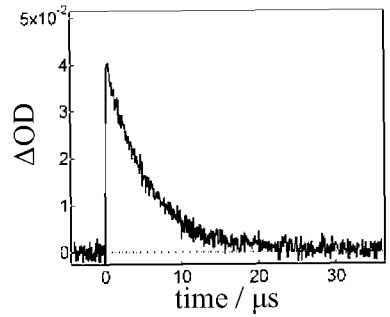
FIG. 7 is a graph showing a decay of absorbing degree in 710 nm for a chromogen of the compound in the embodiment 6, which is measured by a nanosecond laser flash photolysis.

The nanosecond laser flash photolysis measurement processes of 2,3,4',5'-tetrakis(4-methoxy-phenyl)spiro [imidazo [2,1-α]isoindole-5,2'-imidazole] includes: performing the laser flash photolysis measurement of synthesized 2,3,4',5'-tetrakis(4-methoxy-phenyl)spiro [imidazo [2,1-α]isoindole- And FIG. 7 shows the result of measurement of the time decay relating to the absorption band of 710 nm which appears while the 2,3,4',5'-tetrakis(4-methoxyphenyl)spiro [imidazo [2,1-α]isoindole-5,2'-imidazole] benzene solution is irradiated by nanosecond ultraviolet laser having a wavelength of 355 nm (pulse width: 5 ns, output: 4 mJ). As the result, it thus confirms that the chromogen of 2,3,4',5'-tetrakis(4-methoxy-phenyl)spiro [imidazo [2,1-α]isoindole-5,2'-imidazole] has a half-life of 4.2 μs at 25° C. after the irradiation is terminated and is attenuated rapidly. It can also know that the half-life is unchanged even though it is introduced with a methoxy group at the 4,5-position of the imidazole ring.

Figure 8:
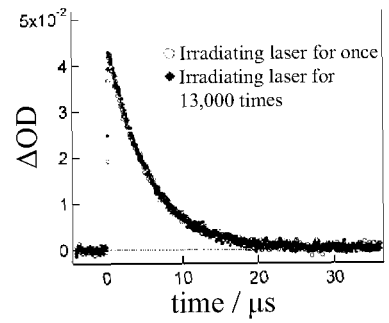
FIG. 8 is a graph showing a decay of absorbing degree in 710 nm for a chromogen in the compound in the embodiment 6, which is measured by irradiating laser pulse for once and irradiating laser pulse for 13,000 times in a measurement of a nanosecond laser flash photolysis.
Figure 9:
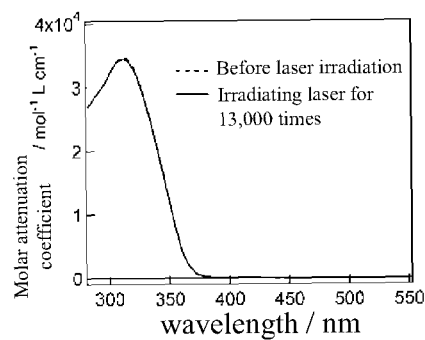
FIG. 9 is a graph showing the UV/visible absorption spectrum, which is obtained by a measurement before laser irradiation and after laser irradiating 13,000 times of the compound in the embodiment 6.

Then it performs the durability test by irradiating the 2,3,4',5'-tetrakis(4-methoxy-phenyl)spiro [imidazo [2,1-α] isoindole-5,2'-imidazole] benzene solution 13000 times by nanosecond ultraviolet laser having a wavelength of 355 nm (pulse width 5 ns, output 4 mJ) at 25° C. FIG. 8 illustrates a result of time decay relating to the absorbance of 710 nm by comparing that is irradiated once by the nanoseconds ultraviolet laser and that is irradiated for 13000 times by the nanoseconds ultraviolet laser. It confirms that the time decay relating to the absorbance is kept remained the same and the sample has not been deteriorated even after being irradiated of 13000 times by nanosecond UV laser. In addition, FIG. 9 illustrates the ultraviolet-visible absorption spectrum of 2,3,4',5'-tetrakis(4-methoxy-phenyl)spiro [imidazo [2,1-α] isoindole-5,2'-imidazole] irradiated once by the nanosecond ultraviolet laser and irradiated for 13000 times by the nanosecond ultraviolet laser. And it thus confirms that the ultraviolet-visible absorption spectrum after the first irradiation and that after irradiated for 13000 times of irradiation are kept unchanged. And the result indicates that 2,3,4',5'-tetrakis(4-methoxy-phenyl)spiro [imidazo [2,1-α]isoindole-5,2'-imidazole] is a photochromic compound having a high repetition durability.

Embodiment 8

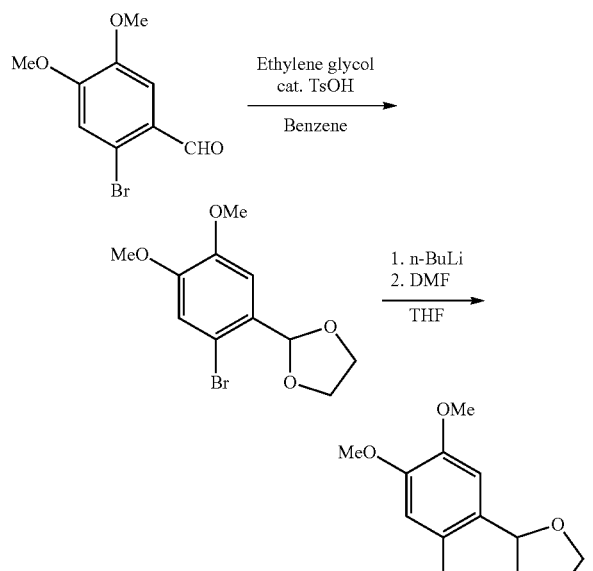

Synthesis of 2-(1,3-dioxolan-2-yl)-4,5-dimethoxybenzaldehyde

The synthesizing processes of the above includes: adding 2-bromo-4,5-dimethoxybenzaldehyde 2.00 g (8.16 mmol), ethylene glycol 1.10 g (17.7 mmol), and p-toluenesulfonic acid monohydrate 140 mg (0.736 mmol), adding benzene 10 mL, then refluxing the mixture for 2 days with Dean-Stark apparatus; after cooling down the temperature to room temperature, terminating the reaction with saturated sodium bicarbonate aqueous solution, and performing extraction with dichloromethane; drying the organic layer with sodium sulfate, and distilling off the solvent under reduced pressure to obtain crude product; and performing a purification with silica gel column chromatography (benzene/ethyl acetate=95/5) to obtain 2-(2-bromo-4,5-dimethoxyphenyl)-1,3-dioxolane 569 mg (1.97 mmol) in 24% yield.

$^1$H NMR (400 MHz, CDCl$_3$): δ=7.11 (s, 1H), 7.02 (s, 1H), 6.00 (s, 1H), 4.20-4.05 (m, 4H), 3.89 (s, 3H), 3.88 (s, 3H)

Dissolving 2-(2-bromo-4,5-dimethoxyphenyl)-1,3-dioxolane 437 mg (1.51 mmol) with dehydrated THF 10 mL and cooling down the mixture to −78° C.; and adding n-butyllithium hexane solution 1.60M hexane solution 1.2 mL slowly, and stirring the mixture for 2 hours at −78° C.; after raising the temperature to −30° C., cooling down the temperature to −78° C. again, and adding dehydration DMF 0.1 mL; then raising temperature to room temperature and stirring the mixture for 12 hours; terminating the reaction with saturated sodium bicarbonate aqueous solution, performing an extraction with ethyl acetate, drying the organic layer with sodium sulfate aqueous solution and distilling off the solvent under reduced pressure to obtain the crude product; and performing recrystallization from hexane/ethyl acetate mixed solvent to obtain 2-(1,3-dioxolan-2-yl)-4,5-dimethoxybenzaldehyde 165 mg (0.693 mmol) in 46% yield.

$^1$H NMR (400 MHz, CDCl$_3$): δ=10.34 (s, 1H), 7.48 (s, 1H), 7.22 (s, 1H), 6.36 (s, 1H), 4.20-4.09 (m, 4H), 3.99 (s, 3H), 3.95 (s, 3H)

Embodiment 9

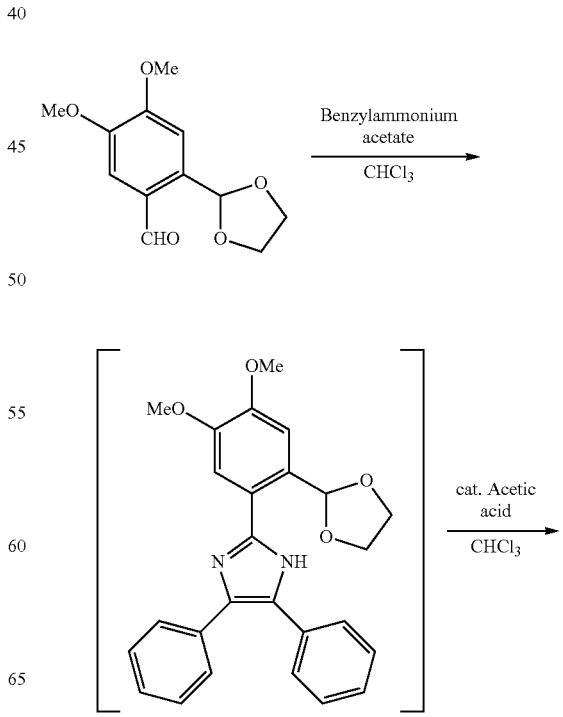

-continued

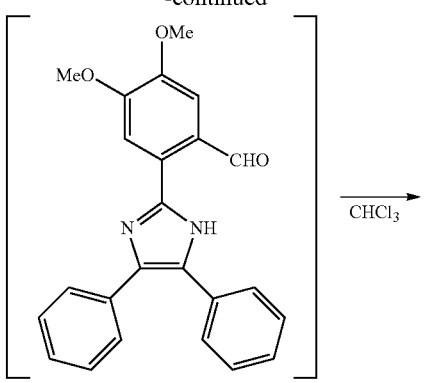

Embodiment 10

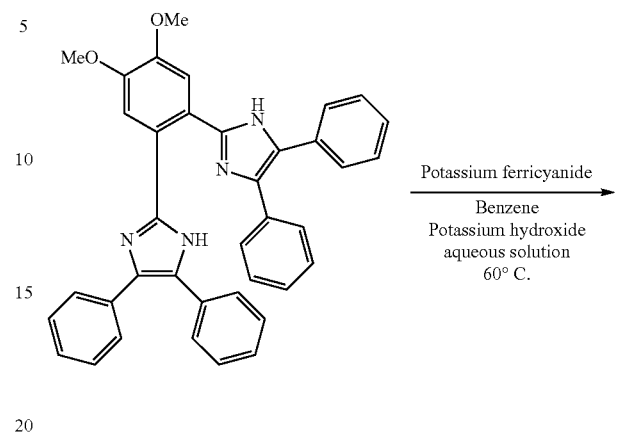

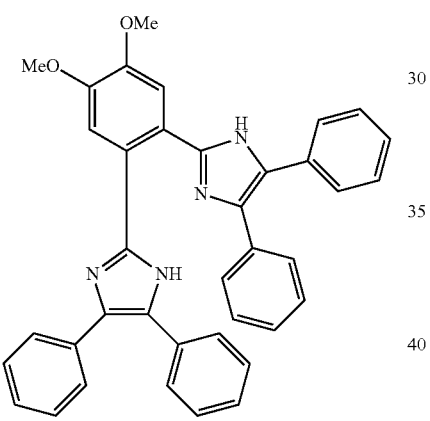

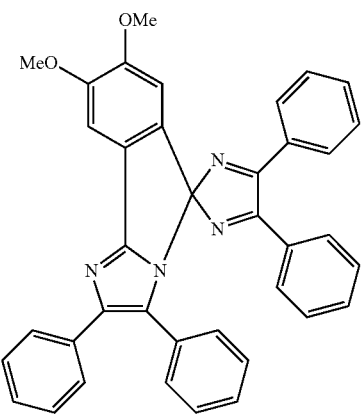

Synthesis of 1,2-bis(4,5-diphenyl-1H-imidazol-2-yl)-4,5-dimethoxybenzene

The synthesizing processes of the above includes: placing 2-(1,3-dioxolan-2-yl)-4,5-dimethoxybenzaldehyde 116 mg (0.487 mmol), benzyl 109 mg (0.518 mmol), ammonium acetate 300 mg (3.89 mmol) and chloroform 3 mL into a sealed tube container, then stirring the mixture for 18 hours at 110° C.; adding acetic acid 1 mL and continuously stirring for an additional 24 hours at 110° C.; neutralizing the mixture with aqueous ammonia, performing an extraction with chloroform, drying the organic layer with sodium sulfate, and distilling off the solvent under reduced pressure to obtain crude product; and performing a recrystallization with chloroform/hexane mixed solvent to obtain 1,2-bis(4,5-diphenyl-1H-imidazol-2-yl)-4,5-dimethoxybenzene 138 mg (0.240 mmol) in 49% yield.

$^1$H NMR (400 MHz, DMSO-d6): δ=14.10 (s, 2H), 7.70 (s, 2H), 7.49-7.47 (m, 4H), 7.39-7.38 (m, 4H), 7.29-7.27 (m, 12H), 3.93 (s, 6H)

Synthesis of 7,8-dimethoxy-2,3,4',5'-tetraphenyl-spiro [imidazo [2,1-α]isoindole-5,2'-imidazole]

The synthesizing processes of the above includes: suspending 1,2-bis(4,5-diphenyl-1H-imidazol-2-yl)-4,5-dimethoxybenzene 54.8 mg (0.0954 Mmol) in benzene 10 mL, dissolving potassium ferricyanide 367 mg (1.11 mmol) and potassium hydroxide 203 mg (3.62 mmol) in ion-exchange water 20 mL and adding it back, then stirring the mixture vigorously for 2 hours at 60° C.; after cooling down the temperature to room temperature, placing the organic layer in a separatory funnel and washing the organic layer well with ion-exchanged water; drying the solvent with sodium sulfate and distilling the solvent off under reduced pressure to obtain the crude product; and using silica gel column chromatography (hexane/ethyl acetate=1/1) to perform a purification to obtain 7,8-dimethoxy-2,3,4',5'-tetraphenyl-spiro [imidazo [2,1-α]isoindole-5,2'-imidazole] 44.0 mg (0.0768 mmol) in 81% yield.

$^1$H NMR (400 MHz, CDCl$_3$): δ=7.59 (s, 1H), 7.56-7.50 (m, 4H), 7.39-7.35 (m, 4H), 7.31-7.28 (m, 6H), 7.23-7.08 (m, 6H), 6.31 (s, 1H), 4.01 (s, 3H), 3.81 (s, 3H). ESI-TOF-MS (m/z): 573 [M+H]$^+$

Embodiment 11

Nanosecond laser flash photolysis measurement of 7,8-dimethoxy-2,3,4',5'-tetraphenylspiro [imidazo [2,1-α]isoindole-5,2'-imidazole]. The nanosecond laser flash photolysis measurement processes of synthesized 7,8-dimethoxy-2,3,4',5'-tetraphenylspiro [imidazo [2,1-α]isoindole-5,2'-imidazole] includes: using a time-resolved spectrometer (model TSP-1000 which is manufactured by KK Yunisoku); using a quartz spectral cell having an optical path length of 10 mm to perform nanosecond laser flash photolysis measurement of 7,8-dimethoxy-2,3,4',5'-tetraphenyl-spiro [imidazo [2,1-α]isoindole-5,2'-imidazole] benzene solution (concentration of $2.6 \times 10^{-4}$M) where it is performed under an argon atmosphere, and 25° C.

Figure 10:
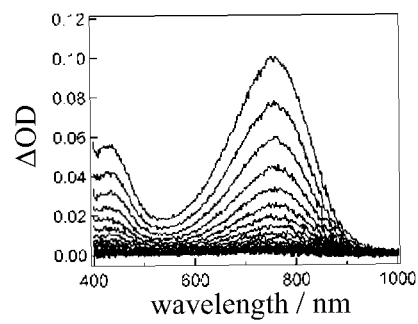
FIG. 10 is a graph showing the visible/near-IR absorption spectrum of time degradation of chromogen of the compound in the embodiment 10, which is measured by a nanosecond laser flash photolysis, wherein the spectrum is obtained by a measurement every 40 μs after the irradiation of a nanosecond laser pulse.

FIG. 10 has shown the results of measurement of visible/near-IR absorption spectrum of 7,8-dimethoxy-2,3,4',5'-tetraphenylspiro [imidazo [2,1-α]isoindole-5,2'-imidazole] benzene solution, wherein the spectrum is obtained by a measurement every 40 μs immediately after the irradiation by using nanosecond laser flash photolysis having a wavelength of 355 nm (pulse width: 5 ns, output: 8 mJ) by means of time-resolved spectroscopy apparatus. From this result, it confirms that the 7,8-dimethoxy-2,3,4',5'-tetraphenylspiro [imidazo [2,1-α]isoindole-5,2'-imidazole] can reversibly generates a chromogen having a strong absorption band of 750 nm. It confirms that the maximum absorption wavelength of the chromogen shifts to the longer wavelength side by introducing two methoxy groups to the 2-position of the aryl group of the imidazole ring.

Figure 11:
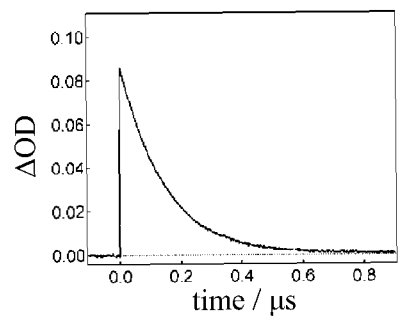
FIG. 11 is a graph showing a decay of absorbing degree in 710 nm for a chromogen of the compound in the embodiment 10, which is measured by a nanosecond laser flash photolysis.

Also, FIG. 11 shows the results of measurement of the time decay relating to the absorption band of 710 nm which appears while the 7,8-dimethoxy-2,3,4',5'-tetraphenylspiro [imidazo [2,1-α]isoindole-5,2'-imidazole] benzene solution is irradiated by nanosecond ultraviolet laser having a wavelength of 355 nm (pulse width: 5 ns, output: 4 mJ)

As the result, it thus confirms that the chromogen of 7,8-dimethoxy-2,3,4',5'-tetraphenylspiro [imidazo [2,1-α]isoindole-5,2'-imidazole] has a half-life of 102 μs after the irradiation is terminated at 25° C. and is attenuated rapidly.

It can also know that the half-life is greatly increased by introducing a methoxy group at the 4,5-position of the imidazole ring.

Figure 12:
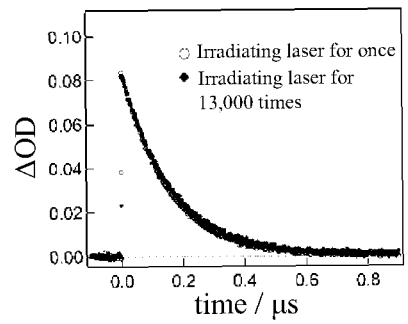
FIG. 12 is a graph showing the a decay of absorbing degree in 710 nm for a chromogen of the compound in the embodiment 10, which is measured by irradiating laser pulse for once and irradiating laser pulse for 13,000 times in a measurement of a nanosecond laser flash photolysis.
Figure 13:
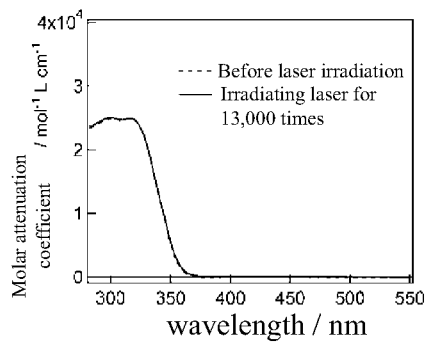
FIG. 13 is a graph showing the UV/visible absorption spectrum, which is obtained by a measurement before laser irradiation and after laser irradiating 13,000 times of the compound in the embodiment 10.

Then it performs the durability test by irradiating the 7,8-dimethoxy-2,3,4',5'-tetraphenylspiro [imidazo [2,1-α]isoindole-5,2'-imidazole] benzene solution 13000 times by nanosecond ultraviolet laser having a wavelength of 355 nm (pulse width; 5 ns, output 4 mJ) at 25° C. FIG. 12 illustrates a result of time decay relating to the absorbance of 710 nm by comparing that is irradiated once by the nanoseconds ultraviolet laser and that is irradiated for 13000 times by the nanoseconds ultraviolet laser. It confirms that the time decay relating to the absorbance is kept remained as the same and the sample has not been deteriorated even after being irradiated of 13000 times by nanosecond UV laser. In addition, FIG. 13 illustrates the ultraviolet-visible absorption spectrum of 7,8-dimethoxy-2,3,4',5'-tetraphenylspiro [imidazo [2,1-α]isoindole-5,2'-imidazole] irradiated once by the nanosecond ultraviolet laser and irradiated 13000 times by the nanosecond ultraviolet laser. And it confirms that the ultraviolet-visible absorption spectrum after the first irradiation and that after 13000 times of irradiation are kept unchanged. And the result indicates that 7,8-dimethoxy-2,3,4',5'-tetraphenylspiro [imidazo [2,1-α]isoindole-5,2'-imidazole] is a photochromic compound having a high repetition durability.

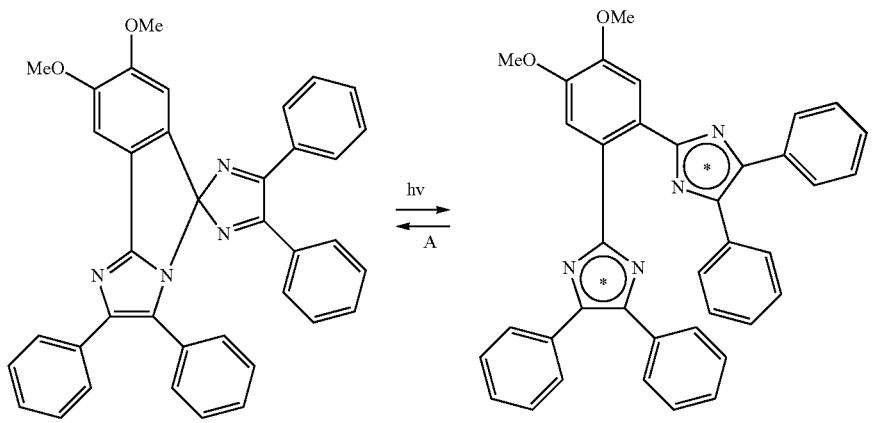

Embodiment 12

Synthesis of 2-(2-(4,5-bis(4-methoxyphenyl)-1H-imidazol-2-yl)phenyl)-4,5-diphenyl-1H-imidazole

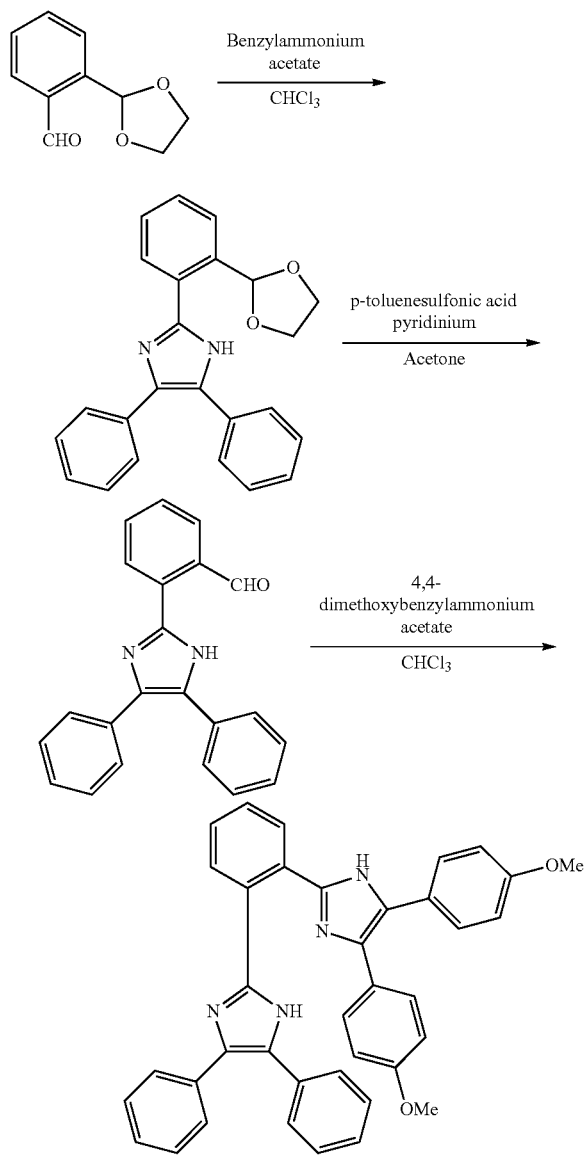

The synthesizing processes of the above includes: placing 2-(1,3-dioxolan-2-yl)benzaldehyde 1.00 g (5.61 mmol), benzyl 1.21 g (5.76 mmol), ammonium acetate 1.59 mg (20.6 mmol) and chloroform 8 mL into a sealed tube container, then stirring for 18 hours at 110° C.; neutralizing with aqueous ammonia, performing an extraction with chloroform, drying the organic layer with sodium sulfate, and distilling off the solvent under reduced pressure to obtain the crude product; and performing a purification with silica gel column chromatography (hexane/ethyl acetate=2/1) to obtain 2-(2-(1,3-dioxolan-2-yl)phenyl)-4,5-diphenyl-1H-imidazole 731 mg (1.94 mmol) in 81% yield.

$^1$H NMR (400 MHz, DMSO-$d_6$): δ=12.59 (s, 1H), 7.97-7.94 (m, 2H), 7.74-7.70 (m, 2H), 7.64-7.23 (m, 9H), 6.85 (s, 1H), 4.09-3.92 (in, 4H)

Dissolving 2-(2-(1,3-dioxolan-2-yl)phenyl)-4,5-diphenyl-1H-imidazole 713 mg (1.94 mmol) in acetone 5 mL, adding p-toluenesulfonic acid pyridinium 176 mg (0.70 mmol) and ion-exchanged water 3 mL, and refluxing the mixture for 2 hours; performing a filtration to collect the solid precipitated after adding ion-exchanged water, washing the solid precipitated well with ion-exchanged water; and performing a purification of 2-(4,5-diphenyl-1H-imidazol-2-yl)benzaldehyde with silica gel column chromatography (hexane/ethyl acetate=2/1) to obtain 410 mg (1.26 mmol) in 65% yield.

$^1$H NMR (400 MHz, CDCl$_3$): δ=13.07 (s, 1H), 10.67 (s, 1H), 8.02 (d, J=7.7 Hz, 1H), 7.87 (d, J=7.2 Hz, 1H), 8.02 ($J_1$=7.5 Hz, $J_2$=7.5 Hz, 1H), 7.60-7.29 (in, 11H)

Placing 2-(4,5-diphenyl-1H-imidazol-2-yl)benzaldehyde 82.9 mg (0.256 mmol), 4,4'-dimethoxybenzyl 75.4 mg (0.256 mmol) and ammonium acetate 172 mg (2.23 mmol) into a sealed tube container, adding acetic acid 3 mL and stirring for 18 hours at 110° C.; and performing a neutralization with aqueous ammonia, performing an extraction with chloroform, drying the organic layer with sodium sulfate and distilling off the solvent under reduced pressure to obtain 2-(2-(4,5-bis(4-methoxyphenyl)-1H-imidazol-2-yl)phenyl)-4,5-diphenyl-1H-imidazole 15.0 mg (0.0261 mmol) in 10% yield.

$^1$H NMR (400 MHz, CDCl$_3$): δ=14.31 (s, 1H), 13.85 (s, 1H), 8.21-6.78 (m, 22H), 3.77 (s, 6H)

Embodiment 13

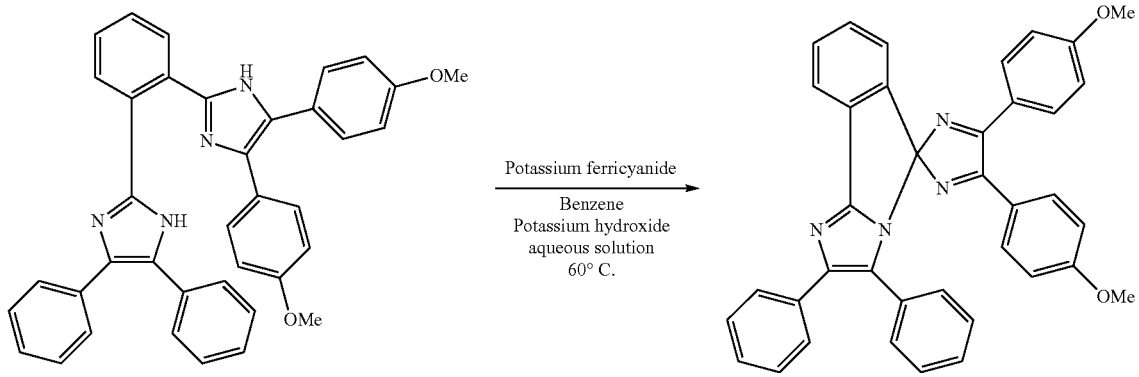 [SMILES: COc1ccc(-c2nc(-c3ccccc3-c3nc(-c4ccccc4)c(-c4ccccc4)[nH]3)[nH]c2-c2ccc(OC)cc2)cc1 ; "BenzenePotassium hydroxideaqueous solution60° C." ; COc1ccc(C2=NC3(N=C2c2ccc(OC)cc2)c2ccccc2-c2nc(-c4ccccc4)c(-c4ccccc4)n23)cc1]

Synthesis of 4',5'-bis(4-methoxyphenyl)-2,3-diphenyl-spiro [imidazo [2,1-α]isoindole-5,2'-imidazole]

The synthesizing processes of the above includes: suspending 2-(2-(4,5-bis(4-methoxyphenyl)-1H-imidazol-2-yl)

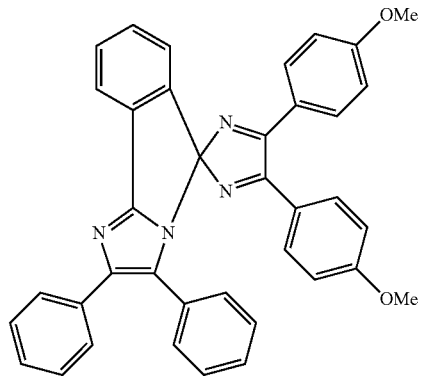 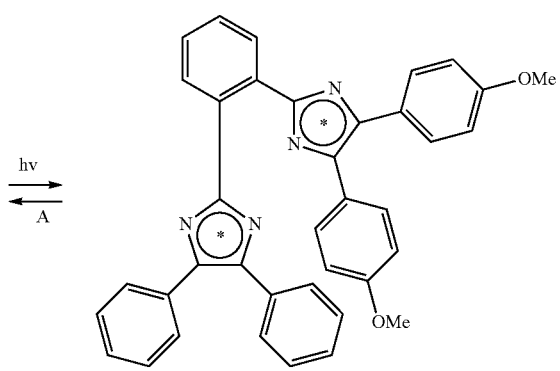

phenyl)-4,5-diphenyl-1H-imidazole 15.0 mg (0.0261 mmol) in benzene 3 mL, and dissolving potassium ferricyanide 354 mg (1.08 mmol) and potassium hydroxide 198 mg (3.53 mmol) in ion-exchange water 20 mL and adding it back, then stirring vigorously for 2 hours at 60° C.; after cooling down the temperature to room temperature, placing the mixture in a separatory funnel and washing the organic layer well with ion-exchanged water; and drying the organic layer with sodium sulfate and distilling the solvent under a reduced pressure to obtain the crude product; and performing a purification with silica gel column chromatography (hexane/ethyl acetate=3/2) to obtain 4',5'-bis(4-methoxyphenyl)-2,3-diphenyl-spiro [imidazo [2,1-α]isoindole-5,2'-imidazole] 11.0 mg (0.0192 mmol) in 74% yield.

$^1$H NMR (400 MHz, CDCl$_3$): δ=8.01 (d, J=7.6 Hz, 2H), 7.64-7.03 (m, 12H), 6.87 (d, J=8.8 Hz, 8H), 3.86 (s, 6H). ESI-TOF-MS (m/z): 573 [M+H]$^+$

Embodiment 14

Nanosecond laser flash photolysis measurement of 4',5'-bis(4-methoxyphenyl)-2,3-diphenyl-spiro [imidazo [2,1-α]isoindole-5,2'-imidazole]

The nanosecond laser flash photolysis measurement processes of synthesized 4',5'-bis(4-methoxyphenyl)-2,3-diphenyl-spiro [imidazo [2,1-α]isoindole-5,2'-imidazole] includes: using time-resolved spectroscopy measuring device (model TSP-1000 which is manufactured by KK Yunisoku); and using a quartz spectral cell having an optical path length of 10 mm to perform nanosecond laser flash photolysis measurement of 4',5'-bis(4-methoxyphenyl)-2,3-diphenyl-spiro [imidazo [2,1-α]isoindole-5,2'-imidazole] benzene solution (concentration of 3.0×10$^{-4}$M) where it is performed under an argon atmosphere and at 25° C.

Figure 14:
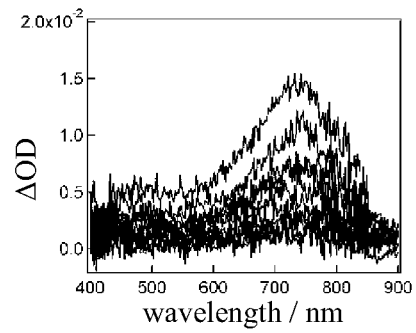
FIG. 14 is a graph showing the visible/near-IR absorption spectrum of time degradation of chromogen of the compound in the embodiment 13, which is measured by nanosecond laser flash photolysis, wherein the spectrum is obtained by a measurement every 0.8 μs after the irradiation of a nanosecond laser pulse.

FIG. 14 shows the results of visible and near infrared absorption spectrum measurement of 4',5'-bis(4-methoxyphenyl)-2,3-diphenyl-spiro [imidazo [2,1-α]isoindole-5,2'-imidazole] benzene solution, wherein the spectrum is obtained by a measurement every 0.8 μs immediately after the irradiation by using nanosecond ultraviolet laser having a wavelength of 355 nm (pulse width: 5 ns, output: 8 mJ) by means of time-resolved spectroscopy apparatus. From this result, it confirms that 4',5'-bis(4-methoxyphenyl)-2,3-diphenyl-spiro [imidazo [2,1-α]isoindole-5,2'-imidazole] can reversibly generates a chromogen having a strong absorption band of 710 nm by irradiation with ultraviolet light.

Figure 15:
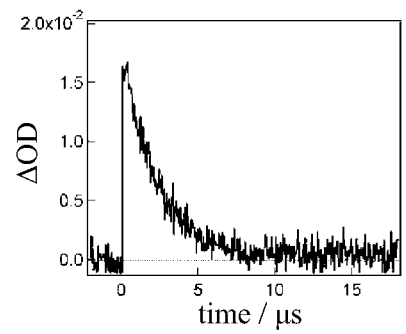
FIG. 15 is a graph showing the a decay of absorbing degree in 710 nm for a chromogen of the compound in the embodiment 13, which is measured by a nanosecond laser flash photolysis.

And FIG. 15 shows the result of measurement of the time decay relating to the absorption band of 710 nm which appears while the 4',5'-bis(4-methoxyphenyl)-2,3-diphenyl-spiro [imidazo [2,1-α]isoindole-5,2'-imidazole] benzene solution is irradiated by nanosecond ultraviolet laser having a wavelength of 355 nm (pulse width: 5 ns, output: 4 mJ). As the result, it thus confirms that the chromogen of 4',5'-bis(4-methoxyphenyl)-2,3-diphenyl-spiro [imidazo [2,1-α]isoindole-5,2'-imidazole] has a half-life of 2.3 μs at 25° C. after the irradiation is terminated, and the chromogen is attenuated rapidly.

Figure 16:
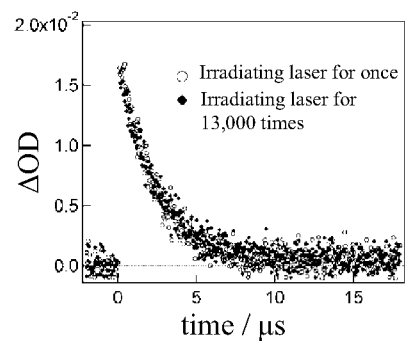
FIG. 16 is a graph showing a decay of absorbing degree in 710 nm for a chromogen of the compound in the embodiment 13, which is measured by irradiating laser pulse for once and irradiating laser pulse for 13,000 times in a measurement of a nanosecond laser flash photolysis
Figure 17:
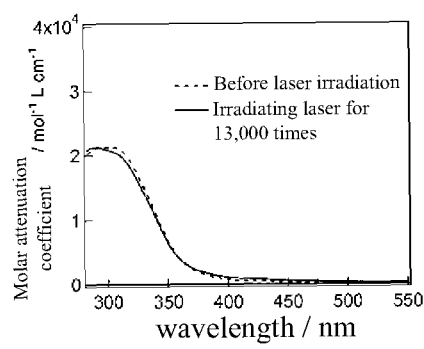
FIG. 17 is a graph showing the UV/visible absorption spectrum, which is obtained by a measurement before laser irradiation and after laser irradiating 13,000 times of the compound in the embodiment 13.

Then it performs the durability test by irradiating the 4',5'-bis(4-methoxyphenyl)-2,3-diphenyl-spiro [imidazo [2,1-α]isoindole-5,2'-imidazole] benzene solution 13000 times by nanosecond ultraviolet laser having a wavelength of 355 nm (pulse width: 5 ns, to be irradiated output: 4 mJ) at 25° C. FIG. 16 illustrates a result of time decay relating to the absorbance of 710 nm by comparing that is irradiated once by the nanoseconds ultraviolet laser and that is irradiated for 13000 times by the nanoseconds ultraviolet laser. It confirms that the time decay relating to the absorbance is kept remained as the same and the sample has not been deteriorated even after being irradiated of 13000 times by nanosecond UV laser. In addition, FIG. 17 illustrates the ultraviolet-visible absorption spectrum of 4',5'-bis(4-methoxyphenyl)-2,3-diphenyl-spiro [imidazo [2,1-α]isoindole-5,2'-imidazole] irradiated once by the nanosecond ultraviolet laser and irradiated 13000 times by the nanosecond ultraviolet laser. And it confirms that the ultraviolet-visible absorption spectrum after the first irradiation and that after 13000 times of irradiation are kept unchanged. And the result indicates that 2,3,4',5'-tetrakis(4-methoxy-phenyl) spiro [imidazo [2,1-α]isoindole-5,2'-imidazole] is a photochromic compound having a high repetition durability.

Embodiment 15

Nanosecond laser flash photolysis measurement of PMMA containing the 2,3,4',5'-tetraphenylspiro [imidazo [2,1-α]isoindole-5,2'-midazole].

The nanosecond laser flash photolysis measurement processes of PMMA containing the 2,3,4',5'-tetraphenylspiro [imidazo [2,1-α]isoindole-5,2'-midazole] includes: dissolving polymethyl methacrylate (PMMA)(manufactured by Aldrich, molecular weight 350,000) 20.2 mg in chloroform 0.4 mL, adding 2,3,4'5'-tetraphenyl-spiro [imidazo [2,1-α]isoindole-5,2'-imidazole] 4.0 mg synthesized in embodiment 3 and adjusting the solution to a concentration of 20 wt %; using the solution to preparing a PMMA film containing the 2,3,4',5'-tetraphenyl-spiro [imidazo [2,1-alpha]isoindole-5,2'-imidazole by casting method; and performing a nanosecond laser flash photolysis measurement on the film at 25° C.

Figure 18:
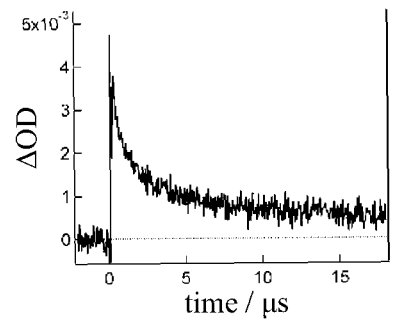
FIG. 18 is a graph showing a decay of absorbing degree in 710 nm for a chromogen of the PMMA film in the embodiment 15, which is measured by a nanosecond laser flash photolysis.

FIG. 18 shows the result of measurement of the time decay relating to the absorption band of 710 nm which appears while PMMA film containing the 2,3,4',5'-tetraphenyl spiro [imidazo [2,1-α]isoindole-5,2'-imidazole] is irradiated by nanosecond ultraviolet laser having wavelength of 355 nm (pulse width: 5 ns, output: 4 mJ). As the result, it thus confirms that the chromogen of 2,3,4',5'-tetraphenyl spiro [imidazo [2,1-α]isoindole-5,2'-imidazole] has a half-life of 3 μs after the irradiation is terminated at 25° C. and is attenuated rapidly even been contained in the solid phase PMMA.

Photochromic material comprising the pentaarylbiimidazole compound of the present invention has a high speed for color switching reaction and high durability as compared to the conventional prior photochromic materials. Moreover, it adjusts a distance, an angle and molecule flexibility of two imidazole rings by use of the number, the type of the substituents and the structure of aromatic ring formed by the substituents binding to the five aryl groups of the compounds of the present invention to thus be possible to appropriately adjust the photochromic characteristics such as color switching reacting speed or coloring density in correspondence to the applying purpose of the compounds as needed in the present invention. Furthermore, the present inventors can also be synthesized with less quantity of procedures and the material used is cheaper, and provides a photochromic compound that can be synthesized at low cost and is industrially-applicable. It can therefore be anticipated that the compound of the present invention will be applied to a wide range of fields such as security ink, light control materials, holographic materials, and optical switch elements.

What is claimed is:
1. A compound represented by the following general formula (1):

in which, in the formula,
the five aryl groups may or may not have substituents $R_A$ to $R_E$,
m is an integer from 1 to 4,
n to q are independent to each other and are integers from 1 to 5,
the substituents $R_A$ are independent to each other and are identical to or different from each other,
wherein the substituent(s) $R_A$ is selected one or more from a group consisting of:
hydrogen atom, halogen atom, nitro group, cyano group, trifluoromethyl group, hydroxyl group, thiol group, amino group, diphenylamino group and carbazole group, and
alkyl group, alkylamino group and alkoxy group with straight chain or with branched chain having carbon number from 1 to 20, and
$—Y_1—SiZ_1Z_2Z_3$ group, $—Y_1—SiY_2Z_1Z_2$ group and $—Y_1—SiY_2Y_3Z_1$ group, wherein $Y_1$ to $Y_3$ and $Z_1$ to $Z_3$ are independent to each other and are identical to or different from each other, and $Y_1$ to $Y_3$ represent alkyl group or alkylene group with straight chain or with branched chain having carbon number from 1 to 20, and $Z_1$ to $Z_3$ represent hydrogen atom or halogen atom or alkoxy group with straight chain or branched chain alkoxy group, and
alicyclic ring, heterocyclic ring and aromatic ring which are mutually bound to form a ring,
the substituents $R_B$ to $R_E$ are independent to each other and are identical to or different from each other, and are substituents with the same definition as the previous substituents $R_A$ and selected one or more substituents from the group consisting of substituent represented by the following structure formula (i):

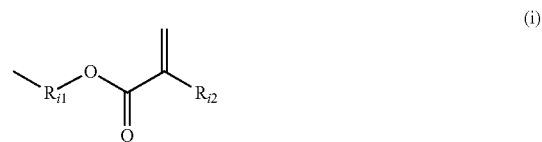

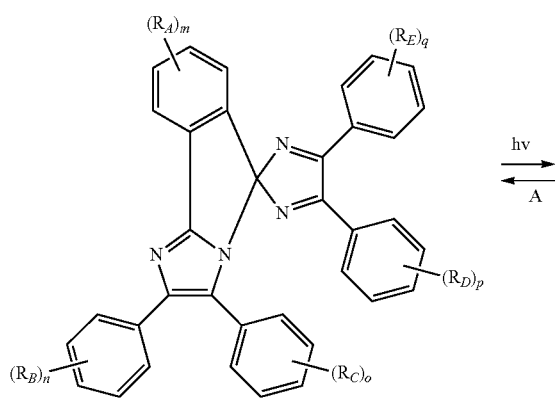 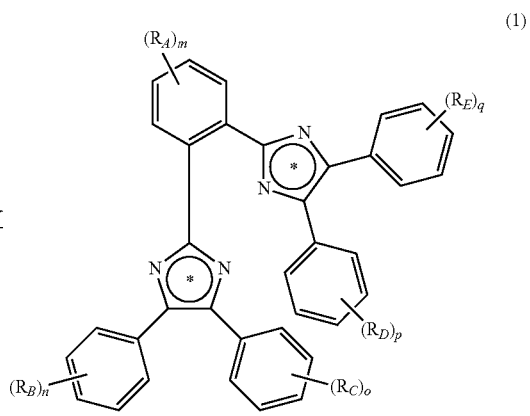

in which, in the formula, $R_{i1}$ is alkylene group or alkoxylene group having carbon number from 1 to 4, $R_{i2}$ is hydrogen atom or alkyl group having carbon number from 1 to 3, the substituent having the aryl group forms together with the binding carbon atom(s) and other substituent(s) to thus form or not form an aliphatic or aromatic ring, in which the ring thereof further may or may not have a substituent with the same definition as the previous substituent having the aryl group.

2. The compound as claimed in claim 1, wherein the structure of a diarylimidazole moiety at one side and the structure of a diarylimidazole moiety at the other side are different and asymmetric to each other.

3. The compound as claimed in claim 2, wherein each substituent $R_A$ to $R_E$ is substituent selected one or more from the group consisting of: hydrogen, methyl group, methoxy group, nitro group and cyano group.

4. A photochromic material comprising the compound as claimed in claim 3.

5. A solvent comprising the compound as claimed in claim 3.

6. A resin comprising the compound as claimed in claim 3.

7. A method for producing the compound as claimed in claim 2, comprising a reaction between a compound and a benzyl derivative having 1,2-diketone, wherein the compound is represented by the following general formula (2), and the benzyl derivative having 1,2-diketone is represented by the following general formula (3) and/or the following general formula (4):

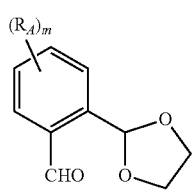
(formula 2)

wherein, in the formula, the aryl group may or may not have substituent $R_A$, and m is an integer from 1 to 4, the substituents $R_A$ are independent to each other and is identical to or different from each other and are substituents with the same definition as the previous substituents $R_A$ in the general formula (1),

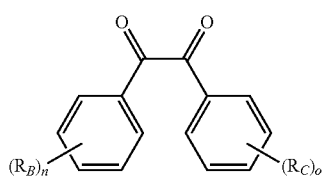
(formula 3)

wherein, in the formula, the two aryl group may or may not have substituents $R_B$ and $R_C$, and n and o are independent to each other, an integer is from 1 to 5, and the substituent $R_B$ and $R_C$ are independent to each other and are identical to or different from each other, and the substituent $R_B$ and $R_C$ are substituents with the same definition as the previous substituents $R_B$ and $R_C$ in the general formula (1),

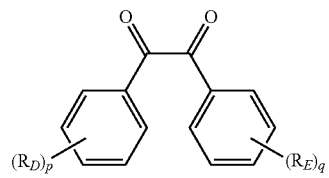
(formula 4)

wherein, in the formula, the two aryl group may or may not have the substituents $R_D$ and $R_E$, and p and q are independent to each other and are integers from 1 to 5, and the substituent $R_D$ and $R_E$ are independent to each other and are identical to or different from each other, and the substituent $R_D$ and $R_E$ are substituents with the same definition as the previous substituents $R_D$ and $R_E$ in the general formula (1).

8. A photochromic material comprising the compound as claimed in claim 2.

9. A solvent comprising the compound as claimed in claim 2.

10. A resin comprising the compound as claimed in claim 2.

11. A method for producing the compound as claimed in claim 2, comprising a reaction between a compound and a benzyl derivative having 1,2-diketone, wherein the compound is represented by the following general formula (2), and the benzyl derivative having 1,2-diketone is represented by the following general formula (3) and/or the following general formula (4):

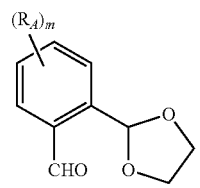
(formula 2)

wherein, in the formula, the aryl group may or may not have substituent $R_A$, and m is an integer from 1 to 4, the substituents $R_A$ are independent to each other and is identical to or different from each other and are substituents with the same definition as the previous substituents $R_A$ in the general formula (1),

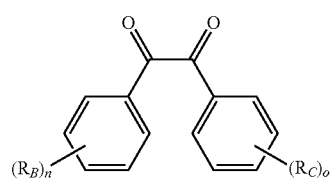
(formula 3)

wherein, in the formula, the two aryl group may or may not have substituents $R_B$ and $R_C$, and n and o are independent to each other, an integer is from 1 to 5, and the substituent $R_B$ and $R_C$ are independent to each other and are identical to or different from each other, and the substituent $R_B$ and $R_C$ are substituents with the same definition as the previous substituents $R_B$ and $R_C$ in the general formula (1), (formula 4)

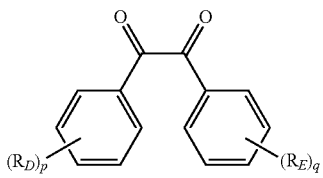

wherein, in the formula, the two aryl group may or may not have the substituents $R_D$ and $R_E$, and p and q are independent to each other and are integers from 1 to 5, and the substituent $R_D$ and $R_E$ are independent to each other and are identical to or different from each other, and the substituent $R_D$ and $R_E$ are substituents with the same definition as the previous substituents $R_D$ and $R_E$ in the general formula (1).

12. The compound as claimed in claim 1, wherein each substituent $R_A$ to $R_E$ is substituent selected one or more from the group consisting of: hydrogen, methyl group, methoxy group, nitro group and cyano group.

13. A photochromic material comprising the compound as claimed in claim 1.

14. A solvent comprising the compound as claimed in claim 1.

15. A resin comprising the compound as claimed in claim 1.

16. A method for producing the compound as claimed in claim 1, comprising a reaction between a compound and a benzyl derivative having 1,2-diketone, wherein the compound is represented by the following general formula (2), and the benzyl derivative having 1,2-diketoneis represented by the following general formula (3) and/or the following general formula (4):

(formula 2)

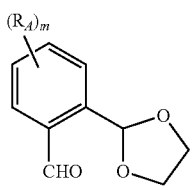

wherein, in the formula, the aryl group may or may not have substituent $R_A$, and m is an integer from 1 to 4, the substituents $R_A$ are independent to each other and is identical to or different from each other and are substituents with the same definition as the previous substituents $R_A$ in the general formula (1), (formula 3)

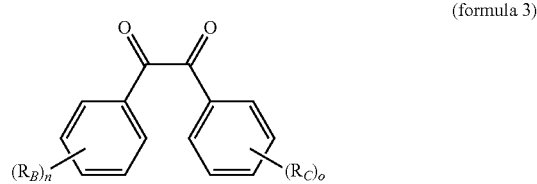

wherein, in the formula, the two aryl group may or may not have substituents $R_B$ and $R_C$, and n and o are independent to each other, an integer is from 1 to 5, and the substituent $R_B$ and $R_C$ are independent to each other and are identical to or different from each other, and the substituent $R_B$ and $R_C$ are substituents with the same definition as the previous substituents $R_B$ and $R_C$ in the general formula (1), (formula 4)

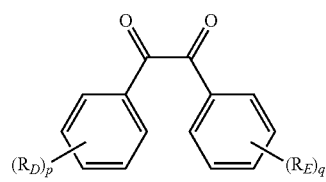

wherein, in the formula, the two aryl group may or may not have the substituents $R_D$ and $R_E$, and p and q are independent to each other and are integers from 1 to 5, and the substituent $R_D$ and $R_E$ are independent to each other and are identical to or different from each other, and the substituent $R_D$ and $R_E$ are substituents with the same definition as the previous substituents $R_D$ and $R_E$ in the general formula (1).

* * * * *